US009409662B2

(12) United States Patent
Zhao et al.

(10) Patent No.: US 9,409,662 B2
(45) Date of Patent: Aug. 9, 2016

(54) FORMULATIONS OF ALBU-BCHE, PREPARATION AND USES THEREOF

(71) Applicants: Qinghai Zhao, North Potomac, MD (US); Xia Luo, Rockville, MD (US); Jason Bock, North Potomac, MD (US)

(72) Inventors: Qinghai Zhao, North Potomac, MD (US); Xia Luo, Rockville, MD (US); Jason Bock, North Potomac, MD (US)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 0 days.

(21) Appl. No.: 14/155,021

(22) Filed: Jan. 14, 2014

(65) Prior Publication Data
US 2014/0199283 A1 Jul. 17, 2014

Related U.S. Application Data

(60) Provisional application No. 61/752,740, filed on Jan. 15, 2013.

(51) Int. Cl.
B65B 3/04 (2006.01)
A61J 1/00 (2006.01)
A61K 38/46 (2006.01)
A61K 38/38 (2006.01)

(52) U.S. Cl.
CPC ... B65B 3/04 (2013.01); A61J 1/00 (2013.01); A61K 38/385 (2013.01); A61K 38/465 (2013.01); C07K 2319/00 (2013.01)

(58) Field of Classification Search
None
See application file for complete search history.

(56) References Cited

U.S. PATENT DOCUMENTS

| 6,001,625 | A | 12/1999 | Broomfield et al. |
| 6,989,261 | B2 | 1/2006 | Watkins et al. |
| 7,045,318 | B2 | 5/2006 | Ballance et al. |
| 7,049,121 | B2 | 5/2006 | Zhan et al. |
| 7,070,973 | B2 | 7/2006 | Lockridge et al. |
| 7,189,690 | B2 | 3/2007 | Rosen et al. |
| 7,438,904 | B1 | 10/2008 | Zhan et al. |
| 7,482,013 | B2 | 1/2009 | Ballance et al. |
| 7,572,764 | B2 | 8/2009 | Cohen et al. |
| 7,731,957 | B1 | 6/2010 | Zhan et al. |
| 8,108,149 | B2 | 1/2012 | Clark et al. |
| 8,211,439 | B2 | 7/2012 | Rosen et al. |
| 8,287,859 | B2 | 10/2012 | Rosen et al. |
| 8,318,156 | B2 | 11/2012 | Landry et al. |
| 8,334,365 | B2 | 12/2012 | Rosen et al. |
| 8,541,373 | B2 | 9/2013 | Sklair-Tavron et al. |
| 2003/0096401 | A1 | 5/2003 | Huse |
| 2003/0153062 | A1 | 8/2003 | Watkins et al. |
| 2004/0016005 | A1 | 1/2004 | Karatzas et al. |
| 2004/0087014 | A1 | 5/2004 | Huse |
| 2004/0120939 | A1 | 6/2004 | Watkins et al. |
| 2004/0121970 | A1 | 6/2004 | Watkins et al. |
| 2004/0147002 | A1 | 7/2004 | Cohen et al. |
| 2004/0168208 | A2 | 8/2004 | Karatzas et al. |
| 2005/0136044 | A1 | 6/2005 | Watkins et al. |
| 2006/0039870 | A1 | 2/2006 | Turner |
| 2006/0063248 | A1 | 3/2006 | Lockridge et al. |
| 2007/0259348 | A1 | 11/2007 | Phadke et al. |
| 2008/0194481 | A1 | 8/2008 | Rosen et al. |
| 2010/0297062 | A1 | 11/2010 | Bock et al. |
| 2011/0002888 | A1 | 1/2011 | Rosen et al. |
| 2013/0108606 | A1 | 5/2013 | Rosen et al. |
| 2014/0162954 | A1 | 6/2014 | Brown et al. |
| 2014/0199286 | A1 | 7/2014 | Zhao et al. |

FOREIGN PATENT DOCUMENTS

| EP | 0 367 090 B1 | 1/1994 |
| EP | 1 832 599 | 9/2007 |
| WO | WO 02/46227 | 6/2002 |
| WO | WO 03/054182 | 7/2003 |
| WO | WO 2007/146038 | 12/2007 |
| WO | WO 2009/058322 | 5/2009 |
| WO | WO 2011/029892 | 3/2011 |
| WO | WO 2011/071926 | 6/2011 |
| WO | WO 2011/071926 A1 | 6/2011 |
| WO | WO 2012/142281 | 10/2012 |
| WO | WO 2014/113359 | 7/2014 |

OTHER PUBLICATIONS

Gao et al. "An albumin-butyrylcholinesterase for cocaine toxicity and addiction: Catalyic and pharmacokinetic properties," Chemico-Biological Interaction, Sep. 25, 2008), vol. 175, pp. 83-87.
International Search Report mailed Apr. 4, 2014 in connection with PCT International Publication No. PCT/US14/11401.
Written Opinion of the International Search Authority mailed Apr. 4, 2014 in connection with PCT International Publication No. PCT/US14/11401.
Frokjaer, Sven, and Daniel E. Otzen (2005) "Protein drug stability: a formulation challenge." Nature Reviews Drug Discovery 4, pp. 298-306.
Gokarn, Yatin R., et al. (2006) "Excipients for protein drugs." Excipient Development for Pharmaceutical, Biotechnology, and Drug Delivery Systems pp. 291-306.
Guidance for Industry: Submission of Summary Bioequivalence Data for ANDAs. U.S. Food and Drug Administration, Center for Drug Evaluation and Research (CDER), Apr. 2009.

(Continued)

Primary Examiner — Paul Holland
(74) Attorney, Agent, or Firm — John P. White; Gary J. Gershik; Cooper & Dunham LLP

(57) ABSTRACT

The present invention provides an aqueous pharmaceutical composition comprising the fusion protein whose amino acid sequence is set forth as SEQ ID No:1 and an aqueous solution comprising 40 to 60 mM sodium phosphate. The present invention further provides a lyophilized pharmaceutical composition, an reconstituted solution, a sealed package comprising the lyophilized pharmaceutical composition, and a vial comprising the lyophilized pharmaceutical or the reconstituted solution. The present invention also provides a method of producing the lyophilized pharmaceutical composition and the sealed package. The present invention also provides a method of treating a human having cocaine seeking behavior, and methods of using the aqueous pharmaceutical composition and lyophilized pharmaceutical composition.

13 Claims, 10 Drawing Sheets

(56) References Cited

OTHER PUBLICATIONS

Krishnamurthy, Rajesh, and Mark C. Manning, (2002) "The stability factor: importance in formulation development." Current Pharmaceutical Biotechnology, 3, Abstract only.

Rathore, Nitin, and Rahul S. Rajan (2008) "Current perspectives on stability of protein drug products during formulation, fill and finish operations." Biotechnology Progress 24, pp. 504-514.

Shire, Steven J. et al. (2004) "Challenges in the development of high protein concentration formulations." Journal of Pharmaceutical Sciences 93, pp. 1390-1402.

Shire, Steven J. (2009) "Formulation and manufacturability of biologics." Current opinion in biotechnology, 20, pp. 708-714.

Wang, Wei. (2000) "Lyophilization and development of solid protein pharmaceuticals." International Journal of Pharmaceutics, 203, pp. 1-60.

Wang, Wei. (2005) "Protein aggregation and its inhibition in biopharmaceutics." International journal of pharmaceutics, 289, pp. 1-30.

Jameel and Hershenson (2010) "Formulation and process development strategies for manufacturing biopharmaceutical", Chapter 20, The impact of buffer on solid state properties and stability of freeze dried dosage forms, p. 511.

Figure 10

```
EDDIIIATKN GKVRGMNLTV FGGTVTAFLG IPYAQPPLGR LRFKKPQSLT KWSDIWNATK        60
YANSCCQNID QSFPGFHGSE MWNPNTDLSE DCLYLNVWIP APKPKNATVL IWIYGGGFQT       120
GTSSLHVYDG KFLARVERVI VVSMNYRVGA LGFLALPGNP EAPGNMGLFD QQLALQWVQK       180
NIAAFGGNPK SVTLFGESSG AASVSLHLLS PGSHSLFTRA ILQSGSFNAP WAVTSLYEAR       240
NRTLNLAKLT GCSRENETEI IKCLRNKDPQ EILLNEAFVV PYGTPLGVNF GPTVDGDFLT       300
DMPDILLELG QFKKTQILVG VNKDEGTWFL VGGAPGFSKD NNSIITRKEF QEGLKIFFPG       360
VSEFGKESIL FHYTDWVDDQ RPENYREALG DVVGDYNFIC PALEFTKKFS EWGNNAFFYY       420
FEHRSSKLPW PEWMGVMHGY EIEFVFGLPL ERRDNYTKAE EILSRSIVKR WANFAKYGNP       480
NETQNNSTSW PVFKSTEQKY LTLNTESTRI MTKLRAQQCR FWTSFFPKVD AHKSEVAHRF       540
KDLGEENFKA LVLIAFAQYL QQCPFEDHVK LVNEVTEFAK TCVADESAEN CDKSLHTLFG       600
DKLCTVATLR ETYGEMADCC AKQEPERNEC FLQHKDDNPN LPRLVRPEVD VMCTAFHDNE       660
ETFLKKYLYE IARRHPFYFA PELLFFAKRY KAAFTECCQA ADKAACLLPK LDELRDEGKA       720
SSAKQRLKCA SLQKFGERAF KAWAVARLSQ RFPKAEFAEV SKLVTDLTKV HTECCHGDLL       780
ECADDRADLA KYICENQDSI SSKLKECCEK PLLEKSHCIA EVENDEMPAD LPSLAADFVE       840
SKDVCKNYAE AKDVFLGMFL YEYARRHPDY SVVLLLRLAK TYETTLEKCC AAADPHECYA       900
KVFDEFKPLV EEPQNLIKQN CELFEQLGEY KFQNALLVRY TKKVPQVSTP TLVEVSRNLG       960
KVGSKCCKHP EAKRMPCAED YLSVVLNQLC VLHEKTPVSD RVTKCCTESL VNRRPCFSAL      1020
EVDETYVPKE FNAETFTFHA DICTLSEKER QIKKQTALVE LVKHKPKATK EQLKAVMDDF      1080
AAFVEKCCKA DDKETCFAEE GKKLVAASQA ALGL                                  1114

(SEQ ID No:1)
```

FORMULATIONS OF ALBU-BCHE, PREPARATION AND USES THEREOF

This application claims the benefit of U.S. Provisional Application No. 61/752,740, filed Jan. 15, 2013, the content of which is hereby incorporated by reference in its entirety.

Throughout this application, various publications are referenced by author and publication date. Full citations for these publications may be found at the end of the specification immediately preceding the claims. The disclosures of these publications are hereby incorporated by reference into this application to describe more fully the art to which this invention pertains.

SEQUENCE LISTING

This application incorporates-by-reference nucleotide and/or amino acid sequences which are present in the file named "140114_2609_84767_A_Sequence_Listing_ACK-.txt," which is 9.64 kilobytes in size, and which was created Jan. 13, 2014 in the IBM-PC machine format, having an operating system compatibility with MS-Windows, which is contained in the text file filed Jan. 14, 2014 as part of this application.

BACKGROUND OF THE INVENTION

Composition 1 represents a novel treatment for cocaine overdose and addiction through a mechanism of specific and rapid cocaine hydrolysis. In Composition 1, the N-terminus of human serum albumin (HSA) has been genetically fused to the C-terminus of the catalytic domain of human butyrylcholinesterase (BChE). Residues 1-529 correspond to the catalytic domain of BChE while the sequence of residues 530-1114 is identical to the mature native form of human serum albumin. A few amino acid substitutions have been introduced within the catalytic domain of BChE to improve the cocaine hydrolytic activity of Composition 1, and the terminal tetramerization domain (45 residues of the C-terminus) has been truncated. The HSA moiety of the fusion protein confers an extended half-life (U.S. Publication No. 2011/0312900 A1).

The previous product formulation contains 30 mg/mL of Composition 1 in 10 mM phosphate, 200 mM mannitol, 60 mM trehalose, and 0.01% polysorbate 80 (PS80), pH 7.2 (PMTT) (U.S. Publication No. 2011/0312900 A1).

SUMMARY OF THE INVENTION

The present invention provides an aqueous pharmaceutical composition comprising the fusion protein whose amino acid sequence is set forth as SEQ ID No:1 and an aqueous solution comprising 40 to 60 mM sodium phosphate.

The present invention further provides a lyophilized pharmaceutical composition comprising the fusion protein whose amino acid sequence is set forth as SEQ ID No:1 and from 0.045 to 0.101 mg sodium phosphate per mg of fusion protein.

The present invention further provides a reconstituted solution comprising the fusion protein whose amino acid sequence is set forth as SEQ ID No:1 and an aqueous solution comprising 40 to 60 mM sodium phosphate, 100 to 150 mM mannitol, 20 to 40 mM trehalose, and 0.02 to 0.05 percent polysorbate 80.

The present invention further provides a sealed package comprising the lyophilized pharmaceutical composition.

The present invention further provides a vial comprising the lyophilized pharmaceutical composition or the reconstituted solution.

The present invention further provides a method of producing the lyophilized pharmaceutical composition, comprising the steps of (i) providing an amount of an aqueous pharmaceutical composition comprising the fusion protein whose amino acid sequence is set forth as SEQ ID No:1 and an aqueous solution comprising 40 to 60 mM sodium phosphate, 100 to 150 mM mannitol, 20 to 40 mM trehalose and 0.02 to 0.05 percent polysorbate 80, and (ii) lyophilizing the amount of the aqueous pharmaceutical composition.

The present invention further provides a method of producing the sealed package, comprising the steps of (i) providing an amount of an aqueous pharmaceutical composition comprising the fusion protein whose amino acid sequence is set forth as SEQ ID No:1 and an aqueous solution comprising 40 to 60 mM sodium phosphate, 100 to 150 mM mannitol, 20 to 40 mM trehalose, and 0.02 to 0.05 percent polysorbate 80, (ii) placing the amount of the aqueous pharmaceutical composition in a container, (iii) lyophilizing the amount of the aqueous pharmaceutical composition, and (iv) sealing the container, thereby forming a sealed package.

The present invention further provides a method of treating a human exhibiting cocaine seeking behavior or concurrently experiencing a biological effect of a single cocaine exposure or of a repeated cocaine exposure, comprising administering to the human an amount of the pharmaceutical composition.

The present invention further provides a method of using the reconstituted solution, comprising administering an amount of the reconstituted solution to a human, thereby attenuating a biological effect of a cocaine exposure.

The present invention further provides a method of using the lyophilized pharmaceutical composition, comprising the steps of (i) reconstituting the lyophilized pharmaceutical composition by adding an amount of a pharmaceutically acceptable solvent to form a reconstituted solution, and (ii) administering an amount of the reconstituted solution to a human, thereby attenuating a biological effect of a cocaine exposure.

The present invention further provides a process for producing a drug product comprising Composition 1, comprising the steps of:
(i) obtaining an amount of aqueous solution comprising Composition 1;
(ii) determining whether the aqueous solution comprising Composition 1 complies with one or more of the acceptance criteria set forth in Table 16;
(iii) qualifying the amount of aqueous solution comprising Composition 1 as acceptable for inclusion in the drug product if it complies with one or more of the acceptance criteria set forth in Table 16; and
(iv) preparing the drug product from the aqueous solution comprising Composition 1 only if it complies with one or more of the acceptance criteria set forth in Table 16.

BRIEF DESCRIPTION OF THE FIGURES

FIG. 10: The amino acid sequence of Composition 1.

DETAILED DESCRIPTION OF THE INVENTION

Figure 1:
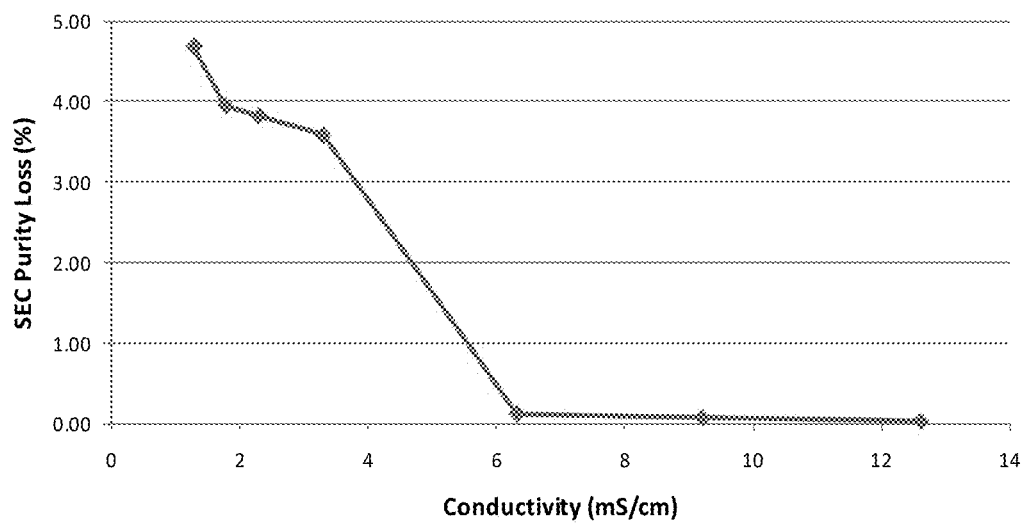
FIG. 1: The effect of ionic strength on the stability of Composition 1 in solution, as determined by NaCl spiking. Composition 1 shows a dramatic increase in stability at conductivities above 6 mS/cm.

As used herein, and unless stated otherwise, each of the following terms shall have the definition set forth below.

As used herein, "effective," as in an amount effective to achieve an end, means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a human exhibiting cocaine-seeking behavior. The specific effective amount will vary with such factors as the age and gender of the human, the particular condition being treated, the physical condition of the human, and the nature of concurrent therapy (if any).

As used herein, "treating" a disorder, condition, or disease shall mean slowing, stopping, inhibiting or reversing the disorder's progression, and/or ameliorating, lessening, alleviating or removing symptoms of the disorder. Thus, treating a disorder encompasses reversing the disorder's progression, including up to the point of eliminating the disorder itself. "Ameliorating" or "alleviating" a disorder, condition, or disease as used herein shall mean to relieve or lessen the symptoms of that disorder, condition, or disease.

As used herein, "first administration" means the first time Composition 1 is administered as part of a course of treatment comprising a series of administrations of Composition 1. In the event that a course of treatment with Composition 1 has been completed or suspended for an interval longer than the usual interval between regularly scheduled administrations, the initial dose of Composition 1 following resumption of regularly scheduled administrations, or initiation of a new course of treatment, is considered a first administration.

As used herein, "a single cocaine exposure" refers to one exposure of cocaine isolated from any other exposure of cocaine. "A recurring cocaine exposure" refers to more than one single cocaine exposure. The recurring cocaine exposure may be a regular or an irregular pattern of single cocaine exposures beginning with the second or subsequent single cocaine exposure in the subject. An individual experiencing recurring cocaine exposure may meet the criteria for cocaine dependence or cocaine abuse of the Diagnostic and Statistical Manual of Mental Disorders IV (DSM-IV).

As used herein, the term "total cocaine exposure" refers to the aggregate cocaine exposure during a given time interval. Total cocaine exposure may be measured during or after a period of a treatment designed to attenuate cocaine seeking behavior or other biological effect of cocaine exposure.

As used herein, the term "a period of cocaine abstinence" refers to a period of time following cocaine exposure where the primate does not experience a new cocaine exposure.

As used herein, the term "relapse" refers to a cocaine exposure following a period of cocaine abstinence.

As used herein, "reconstituted solution" means a solution produced by dissolving a lyophilized substance in an amount of solvent. In an embodiment, the solvent is water for injection (WFI). In an embodiment, the volume of solvent used is the volume of pre-lyophilization solution used to make the lyophilized substance. In an embodiment, the volume of solvent used is more than the volume of pre-lyophilization solution used to make the lyophilized substance. In an embodiment, the volume of solvent used is 110 percent more than the volume of pre-lyophilization solution used to make the lyophilized substance. In an embodiment, the volume of solvent used is less than the volume of pre-lyophilization solution used to make the lyophilized substance.

As used herein, "purity," as in purity of a pharmaceutical composition comprising Composition 1, refers to the relative amount of Composition 1 that is not disintegrated, monomeric, and in its native conformation. Purity may be measured by size exclusion high performance liquid chromatography (SE-HPLC), hydrophobic interaction high performance liquid chromatography (HI-HPLC), sodium dodecylsylfate polyacramide gel electrophoresis (SDS-PAGE), or any other method known in the art, and may be expressed as a percentage. As used herein, "recommended conditions," or "recommended storage conditions" as in a sample stored at the recommended conditions, means the storage conditions determined to keep the characteristics of the composition within acceptable parameters for the duration of storage. In specific embodiments, the recommended storage conditions are a temperature of 2-8° C., an upright position, and/or minimal light exposure.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2 . . . 49 mg unit amounts are included as embodiments of this invention.

The present invention provides an aqueous pharmaceutical composition comprising the fusion protein whose amino acid sequence is set forth as SEQ ID No:1 and an aqueous solution comprising 40 to 60 mM sodium phosphate. In an embodiment, the sodium phosphate comprises 13 to 19 mM sodium phosphate monobasic. In an embodiment, the sodium phosphate comprises 28 to 41 mM sodium phosphate dibasic.

In an embodiment, the aqueous solution further comprises one or more of 100 to 150 mM mannitol, 20 to 40 mM trehalose, or 0.02 to 0.05 percent polysorbate 80. In an embodiment, the aqueous solution comprises 50 mM sodium phosphate, 115 mM mannitol, 35 mM trehalose, and 0.03 percent polysorbate 80. In an embodiment, the aqueous solution comprises 60 mM sodium phosphate, 100 mM mannitol, 30 mM trehalose, and 0.03 percent polysorbate 80. In an embodiment, the sodium phosphate comprises 16 mM sodium phosphate monobasic and 34 mM sodium phosphate dibasic.

In an embodiment, the aqueous pharmaceutical composition comprises the fusion protein, 2.2 mg/ml sodium phosphate monobasic, 4.9 mg/ml sodium phosphate dibasic, 21 mg/ml mannitol, 13 mg/ml trehalose, and 0.3 mg/ml polysorbate 80.

In an embodiment, the concentration of the fusion protein is 80 to 120 mg/ml. In an embodiment, the concentration of the fusion protein is 110 mg/ml. In an embodiment, the concentration of the fusion protein is 100 mg/ml. In an embodiment, the osmolality of the aqueous pharmaceutical composition is from 250 to 350 mOsm/kg. In an embodiment, the osmolality of the aqueous pharmaceutical composition is from 275 to 325 mOsm/kg. In an embodiment, the osmolality of the aqueous pharmaceutical composition is 300 mOsm/kg.

In an embodiment, the aqueous pharmaceutical composition has a pH of 6.9-7.5. In an embodiment, the aqueous pharmaceutical composition has a pH of 7.1-7.3. In an embodiment, the aqueous pharmaceutical composition has a pH of 7.2.

In an embodiment, the purity of the fusion protein decreases by 4 percent or less after incubation at 25° C. for 6 days. In an embodiment, the purity of the fusion protein decreases by 2.5 percent or less after incubation at 25° C. for 6 days. In an embodiment, the purity of the fusion protein decreases by 1.0 percent or less after incubation at 25° C. for 6 days. In an embodiment, the purity of the fusion protein decreases by 0.5 percent or less after incubation at 25° C. for 6 days.

In an embodiment, the proportion of the fusion protein in unaggregated form decreases by 4 percent or less after incubation at 25° C. for 6 days. In an embodiment, the proportion of the fusion protein in unaggregated form decreases by 2.5 percent or less after incubation at 25° C. for 6 days. In an embodiment, the proportion of the fusion protein in unaggregated form decreases by 1.0 percent or less after incubation at 25° C. for 6 days. In an embodiment, the proportion of the fusion protein in unaggregated form decreases by 0.5 percent or less after incubation at 25° C. for 6 days.

In an embodiment, the purity of the fusion protein decreases by 5 percent or less after 6 to 10 freeze-thaw cycles. In an embodiment, the purity of the fusion protein decreases by 2.5 percent or less after 6 to 10 freeze-thaw cycles. In an embodiment, the purity of the fusion protein decreases by 0.1, 0.3, 0.5, 1.0, 1.5 or 2.0 percent or less after 6 to 10 freeze-thaw cycles.

In an embodiment, the proportion of the fusion protein in unaggregated form decreases by 5 percent or less after 6 to 10 freeze-thaw cycles. In an embodiment, the proportion of the fusion protein in unaggregated form decreases by 2.5 percent or less after 6 to 10 freeze-thaw cycles. In an embodiment, the proportion of the fusion protein in unaggregated form decreases by 0.1, 0.3, 0.5, 1.0, 1.5 or 2.0 percent or less after 6 to 10 freeze-thaw cycles.

The present invention further provides a lyophilized pharmaceutical composition produced by a process which comprises lyophilizing the aqueous pharmaceutical composition.

The present invention further provides a lyophilized pharmaceutical composition comprising the fusion protein whose amino acid sequence is set forth as SEQ ID No:1 and from 0.045 to 0.101 mg sodium phosphate per mg of fusion protein. In an embodiment, the sodium phosphate comprises 0.014 to 0.031 mg sodium phosphate monobasic per mg of fusion protein. In an embodiment, the sodium phosphate comprises 0.031 to 0.07 mg sodium phosphate dibasic per mg of fusion protein.

In an embodiment, the sodium phosphate comprises 0.051 to 0.077 mg sodium phosphate per mg of fusion protein. In an embodiment, the sodium phosphate comprises 0.056 to 0.085 mg sodium phosphate per mg of fusion protein. In an embodiment, the sodium phosphate comprises 0.059 to 0.09 mg sodium phosphate per mg of fusion protein.

In an embodiment, the sodium phosphate comprises 0.016 to 0.024 mg sodium phosphate monobasic per mg of fusion protein. In an embodiment, the sodium phosphate comprises 0.018 to 0.026 mg sodium phosphate monobasic per mg of fusion protein. In an embodiment, the sodium phosphate comprises 0.0183 to 0.0275 mg sodium phosphate monobasic per mg of fusion protein.

In an embodiment, the sodium phosphate comprises 0.035 to 0.053 mg sodium phosphate dibasic per mg of fusion protein. In an embodiment, the sodium phosphate comprises 0.039 to 0.058 mg sodium phosphate dibasic per mg of fusion protein. In an embodiment, the sodium phosphate comprises 0.040 to 0.061 mg sodium phosphate dibasic per mg of fusion protein.

In an embodiment, the lyophilized pharmaceutical composition further comprises one or more of 0.146 mg to 0.369 mg mannitol per mg of fusion protein, 0.061 to 0.182 mg trehalose per mg of fusion protein, or 0.0016 to 0.00594 mg polysorbate 80 per mg of the fusion protein.

In an embodiment, the lyophilized pharmaceutical composition further comprises one or more of 0.146 mg to 0.328 mg mannitol per mg of fusion protein, 0.061 to 0.182 mg trehalose per mg of fusion protein, or 0.0016 to 0.00594 mg polysorbate 80 per mg of the fusion protein.

In an embodiment, the lyophilized pharmaceutical composition further comprises one or more of 0.166 mg to 0.248 mg mannitol per mg of fusion protein, 0.069 to 0.138 mg trehalose per mg of fusion protein, or 0.0018 to 0.0045 mg polysorbate 80 per mg of the fusion protein. In an embodiment, the lyophilized pharmaceutical composition further comprises one or more of 0.183 mg to 0.273 mg mannitol per mg of fusion protein, 0.076 to 0.152 mg trehalose per mg of fusion protein, or 0.002 to 0.00495 mg polysorbate 80 per mg of the fusion protein. In an embodiment, the lyophilized pharmaceutical composition further comprises one or more of 0.175 mg to 0.369 mg mannitol per mg of fusion protein, 0.110 to 0.166 mg trehalose per mg of fusion protein, or 0.0025 to 0.0038 mg polysorbate 80 per mg of the fusion protein.

In an embodiment, the lyophilized pharmaceutical composition comprises the fusion protein, 0.0705 mg sodium phosphate, 0.2095 mg mannitol, 0.1324 mg trehalose, and 0.003 mg polysorbate 80 per mg of the fusion protein.

In an embodiment, the amount of the fusion protein is 80 to 120 mg. In an embodiment, the amount of the fusion protein is 110 mg. In an embodiment, the amount of the fusion protein is 100 mg.

In an embodiment, the time required to reconstitute the lyophilized pharmaceutical composition in sterile water for injection is 4 minutes or less. In an embodiment, the time required to reconstitute the lyophilized pharmaceutical composition in sterile water for injection is 5, 6, 7, 8, 9 or 10 minutes or less.

In an embodiment, the time required to reconstitute the lyophilized pharmaceutical composition in sterile water for injection after one month of storage is 6 minutes or less. In an embodiment, the time required to reconstitute the lyophilized pharmaceutical composition in sterile water for injection after one month of storage is 7, 8, 9, 10, 11 or 12 minutes or less.

In an embodiment, the residual moisture is 3 percent or less. In an embodiment, the residual moisture is 0.1, 0.3, 0.4, 0.5, 1 or 2 percent or less.

The present invention further provides a reconstituted solution produced by a process which comprises reconstituting the lyophilized pharmaceutical composition with a pharmaceutically acceptable solvent.

In an embodiment, the pharmaceutically acceptable solvent is water for injection.

The present invention further provides a reconstituted solution comprising the fusion protein whose amino acid sequence is set forth as SEQ ID No:1 and an aqueous solution comprising 40 to 60 mM sodium phosphate, 100 to 150 mM mannitol, 20 to 40 mM trehalose, and 0.02 to 0.05 percent polysorbate 80.

In an embodiment, the reconstituted solution comprises 50 mM sodium phosphate, 115 mM mannitol, 35 mM trehalose, and 0.03 percent polysorbate 80.

In an embodiment, the reconstituted solution comprises the fusion protein, 2.2 mg/ml sodium phosphate monobasic, 4.9 mg/ml sodium phosphate dibasic, 21 mg/ml mannitol, 13 mg/ml trehalose, and 0.3 mg/ml polysorbate 80.

In an embodiment, the osmolality of the reconstituted solution is from 250 to 350 mOsm/kg. In an embodiment, the osmolality of the reconstituted solution is from 275 to 325 mOsm/kg. In an embodiment, the osmolality of the reconstituted solution is 300 mOsm/kg.

In an embodiment, the reconstituted solution has a pH of 6.9-7.5. In an embodiment, the reconstituted solution has a pH of 7.1-7.3. In an embodiment, the reconstituted solution has a pH of 7.2.

The present invention further provides a sealed package comprising the lyophilized pharmaceutical composition.

In an embodiment, the sealed package comprises 80-120 mg of fusion protein. In an embodiment, the sealed package comprises 100-110 mg of fusion protein.

In an embodiment, the pharmaceutical composition is stable under recommended storage conditions for at least 6-36 months. In an embodiment, the pharmaceutical composition is stable under recommended storage conditions for at least 6 months. In an embodiment, the pharmaceutical composition is stable under recommended storage conditions for at least 9, 12, 18, 24 or 36 months. In a specific embodiment, the pharmaceutical composition meets or exceeds 1, 2, 3, 4, 5 or more of the stability parameters set forth in Table 17. In a specific embodiment, the pharmaceutical composition meets or exceeds 1, 2, 3, 4, 5 or more of the stability parameters set forth in Table 18. In a specific embodiment, the pharmaceutical composition meets or exceeds 1, 2, 3, 4, 5 or more of the stability parameters set forth in Table 19.

In an embodiment, the purity of the fusion protein remains at 99.0% or more after storage for six months at 2-8° C.

In an embodiment, the purity of the fusion protein remains at 96.0% or more after storage for six months at 25° C.

In an embodiment, the purity of the fusion protein remains at 89.0% or more after storage for six months at 40° C.

In an embodiment, the purity of the fusion protein remains at 98.0% or more after storage for 12 months at 2-8° C.

In an embodiment, the purity of the fusion protein remains at 95.0% or more after storage for 12 months at 25° C.

The present invention further provides a vial comprising the lyophilized pharmaceutical composition or the reconstituted solution.

In an embodiment, the lyophilized pharmaceutical composition or reconstituted solution comprises from 80 to 120 mg of the fusion protein. In an embodiment, the lyophilized pharmaceutical composition or reconstituted solution comprises from 90 to 110 mg of the fusion protein. In an embodiment, the lyophilized pharmaceutical composition or reconstituted solution comprises 100 mg of the fusion protein.

The present invention further provides a method of producing a lyophilized pharmaceutical composition, comprising the steps of (i) obtaining an amount of the pharmaceutical composition, and (ii) lyophilizing the amount of the pharmaceutical composition.

The present invention further provides a method of producing the lyophilized pharmaceutical composition, comprising the steps of (i) obtaining an amount of an aqueous pharmaceutical composition comprising the fusion protein whose amino acid sequence is set forth as SEQ ID No:1 and an aqueous solution comprising 40 to 60 mM sodium phosphate, 100 to 150 mM mannitol, 20 to 40 mM trehalose and 0.02 to 0.05 percent polysorbate 80, and (ii) lyophilizing the amount of the pharmaceutical composition.

The present invention further provides a method of producing a sealed package comprising a lyophilized pharmaceutical composition, comprising the steps of (i) obtaining an amount of the pharmaceutical composition, (ii) placing the amount of the pharmaceutical composition in a container, (iii) lyophilizing the amount of the pharmaceutical composition, and (iv) sealing the container, thereby forming a sealed package.

The present invention further provides a method of producing the sealed package, comprising the steps of (i) obtaining an amount of an aqueous pharmaceutical composition comprising the fusion protein whose amino acid sequence is set forth as SEQ ID No:1 and an aqueous solution comprising 40 to 60 mM sodium phosphate, 100 to 150 mM mannitol, 20 to 40 mM trehalose and 0.02 to 0.05 percent polysorbate 80, (ii) placing the amount of the pharmaceutical composition in a container, (iii) lyophilizing the amount of the pharmaceutical composition, and (iv) sealing the container, thereby forming a sealed package.

In an embodiment, the lyophilizing comprises cooling the pharmaceutical composition to a temperature less than −17° C. In an embodiment, the lyophilizing comprises cooling the pharmaceutical composition to a temperature less than −29° C.

In an embodiment, the lyophilizing comprises cooling the pharmaceutical composition to a temperature less than −45° C. In an embodiment, the lyophilizing comprises cooling the pharmaceutical composition to a temperature from −17° C. to −45° C.

In an embodiment, the lyophilizing is achieved using a lyophilizer unit with pre-cooled product shelves.

In an embodiment, the lyophilizing comprises annealing the pharmaceutical composition before primary drying.

In an embodiment, the annealing comprises holding the temperature at −10° C. or less for 2 to 8 hours. In an embodiment, the annealing comprises holding the temperature at −18° C., −17° C., −16° C., −15° C., −14° C., −13° C., −12° C., −11° C. or −10° C. for 2 to 8 hours. In an embodiment, the annealing comprises holding the temperature at −18° C. for 5 hours.

In an embodiment, the lyophilizing comprises placing a container holding an amount of the composition on a shelf held at 5° C., holding the temperature at 5° C. for 2 hours, reducing the temperature to −45° C. at a rate of −0.3° C. per minute, holding the temperature at −45° C. for 3 hours, increasing the temperature to −18° C. at a rate of 0.8° C. per minute, holding the temperature at −18° C. for 5 hours, reducing the temperature to −45° C. at a rate of 0.3° C. per minute, holding the temperature at −45° C. for 2 hours, reducing the pressure to 100 mT, holding the shelf temperature at −45° C. for 1 hour, increasing the shelf temperature to −10° C. at a rate of 0.6° C. per minute, holding the shelf temperature at −10° C. for 36 hours, increasing the shelf temperature to 25° C. at a rate of 0.6° C. per minute, holding the shelf temperature at 25° C. for 15 hours, and restoring the chamber to partial atmospheric pressure.

In an embodiment, the lyophilizing comprises placing a container holding an amount of the composition on a shelf held at 5° C., holding the temperature at 5° C. for 1-3 hours, reducing the temperature to −45° C. at a rate of −0.3° C. per minute, holding the temperature at −45° C. for 2-4 hours, increasing the temperature to −10° C. or less at a rate of 0.8° C. per minute, holding the temperature at such temperature for 4-6 hours, reducing the temperature to −45° C. at a rate of 0.3° C. per minute, holding the temperature at −45° C. for 1-3 hours, reducing the pressure to 100-500 mT, holding the shelf temperature at −45° C. for 1 hour or more, increasing the shelf temperature to −10° C. at a rate of 0.6° C. per minute, holding the shelf temperature at −10° C. for 36 hours, increasing the shelf temperature to 25° C. or more at a rate of 0.6° C. per minute, holding the shelf temperature at such temperature for 15 hours, and restoring the chamber to partial atmospheric pressure.

In an embodiment, the container is a vial.

In an embodiment, the vial is made of glass. In an embodiment, the vial is made of USP Type 1 glass. In an embodiment, the container is made of flint glass.

In an embodiment, the vial is closed by a stopper. In an embodiment, the stopper is sealed by an aluminum seal. In an embodiment, the stopper has a FLUROTEC™ coating.

In an embodiment, the volume of the vial is from 1.5 to 5 ml. In an embodiment, the volume of the vial is 3 ml.

In an embodiment, the sealing comprises inserting a stopper. In an embodiment, the stopper is elastomeric. In an embodiment, the stopper comprises rubber. In an embodiment, the stopper comprises butyl rubber. In an embodiment, the stopper is halogenated. In an embodiment, the stopper comprises chlorobutyl rubber. In an embodiment, the stopper is coated with a coating. In an embodiment, the coating is FLUROTEC™.

The present invention further provides a method of using the aqueous pharmaceutical composition, comprising administering an amount of the composition to a human, thereby attenuating a biological effect of a cocaine exposure.

The present invention further provides a method of using the lyophilized pharmaceutical composition, comprising the steps of (i) reconstituting the lyophilized pharmaceutical composition by adding an amount of a pharmaceutically acceptable solvent to form a reconstituted solution, and (ii) administering an amount of the reconstituted solution to a human, thereby attenuating a biological effect of a cocaine exposure.

The present invention further provides a method of using the reconstituted solution, comprising administering an amount of the reconstituted solution to a human, thereby attenuating a biological effect of a cocaine exposure.

The present invention further provides a method of using the sealed package, comprising the steps of (i) adding an amount of a pharmaceutically acceptable solvent to the sealed package, thereby reconstituting the lyophilized pharmaceutical to form a reconstituted solution, (ii) removing an amount of the reconstituted solution from the sealed package, and (iii) administering the amount of the reconstituted solution to a human, thereby attenuating a biological effect of a cocaine exposure.

In an embodiment, the human exhibits cocaine-seeking behavior. In an embodiment, the human is concurrently using cocaine. In an embodiment, the human is concurrently abusing cocaine. In an embodiment, the human is concurrently experiencing a period of cocaine abstinence. In an embodiment, the human has experienced at least one prior single cocaine exposure. In an embodiment, the human has experienced recurring cocaine exposure. In an embodiment, the human is concurrently experiencing recurring cocaine exposure. In an embodiment, the human is concurrently experiencing cocaine dependence. In an embodiment, the human has experienced cocaine dependence. In an embodiment, the human has experienced relapse. In an embodiment, the human is concurrently experiencing recurring cocaine exposure following relapse.

In an embodiment, the human is seeking treatment for cocaine abuse. In an embodiment, the human is seeking treatment for cocaine dependence.

In an embodiment, the human has overdosed on cocaine.

The present invention further provides a method of treating a human exhibiting cocaine seeking behavior or concurrently experiencing a biological effect of a single cocaine exposure or of a repeated cocaine exposure, comprising administering to the human an amount of the composition.

In an embodiment, the amount of the composition is from 50 to 300 mg of fusion protein. In an embodiment, the amount of the composition is 100, 150 or 300 mg of fusion protein.

In an embodiment, the administering is repeated weekly. In an embodiment, the administering is repeated twice a week. In an embodiment, the administering is repeated every two weeks.

In an embodiment, the treating is inducing abstinence from cocaine in the human for a time period of at least three weeks beginning ten weeks after the first administration of the composition to the human.

In an embodiment, the treating is inducing a reduction in the number of times the human uses cocaine during a time period of at least seven weeks beginning five weeks after the first administration of the composition to the human according to the method, as compared to the number of times the human used cocaine during the seven week period immediately prior to the first administration of the composition to the human. In an embodiment, the treating is inducing abstinence from cocaine in the human for a time period of at least seven weeks beginning five weeks after the first administration of the composition to the human.

In an embodiment, the treating is inducing a reduction in the number of times the human uses cocaine during a time period of at least seven weeks beginning five weeks after the first administration of the composition to the human according to the method, as compared to the number of times the human used cocaine during the seven week period immediately prior to the first administration of the composition to the human, wherein the human provides a urine sample at a regular interval and the number of times the human uses cocaine is determined by the number of times the human's urine tests positive for cocaine metabolites.

In an embodiment, the regular interval is three times per week.

In an embodiment, testing positive for cocaine metabolites is having more than 150 ng benzoylecgonine or more than 15 ng ecgonine methyl ester per ml of urine.

In an embodiment, the treating is reducing the human's cocaine craving, as measured by the Brief Substance Craving Scale.

In an embodiment, the treating is improving the human's Clinical Global Impression of disease severity, as assessed by the human and/or another observer twelve weeks after the first administration of the composition to the human.

In an embodiment, the treating is improving the human's Clinical Global Impression of disease change, as assessed by the human and/or another observer twelve weeks after the first administration of the composition to the human.

In an embodiment, the treating is improving the human's Social Adjustment Scale twelve weeks after the first administration of the composition to the human.

In an embodiment, the treating is improving the human's Addiction Severity Index twelve weeks after the first administration of the composition to the human.

In an embodiment, the treating is improving the human's Short Form Health Survey twelve weeks after the first administration of the composition to the human.

In an embodiment, the treating is attenuating a biological effect of a cocaine exposure in the human.

In an embodiment, the biological effect is cocaine seeking behavior.

In an embodiment, the administering is administering by intramuscular injection.

The present invention further provides a process for producing a drug product comprising Composition 1, comprising the steps of:
  (i) obtaining an amount of aqueous solution comprising Composition 1;
  (ii) determining whether the aqueous solution comprising Composition 1 complies with one or more of the acceptance criteria set forth in Table 16;
  (iii) qualifying the amount of aqueous solution comprising Composition 1 as acceptable for inclusion in the drug product if it complies with one or more of the acceptance criteria set forth in Table 16; and
  (iv) preparing the drug product from the aqueous solution comprising Composition 1 only if it complies with one or more of the acceptance criteria set forth in Table 16.

In an embodiment, in step (ii) the determining is repeated for each of the acceptance criteria set forth in Table 16, in step (iii) qualifying the amount of aqueous solution comprising Composition 1 as acceptable for inclusion in the drug product if it complies with all the acceptance criteria set forth in Table 16; and in step (iv) preparing the drug product from the aqueous solution comprising Composition 1 only if it complies with all the acceptance criteria set forth in Table 16.

The specific embodiments and examples described herein are illustrative, and many variations can be introduced on these embodiments and examples without departing from the spirit of the disclosure or from the scope of the appended claims. Elements and/or features of different illustrative embodiments and/or examples may be combined with each other and/or substituted for each other within the scope of this disclosure and appended claims.

For the foregoing embodiments, each embodiment disclosed herein is contemplated as being applicable to each of the other disclosed embodiment.

All combinations and sub-combinations of each of the various elements of the methods and embodiments described herein are envisaged and are within the scope of the invention.

This invention will be better understood by reference to the Examples which follow, which are set forth to aid in an understanding of the subject matter but are not intended to, and should not be construed to, limit in any way the claims which follow thereafter.

EXAMPLES

Example 1

Experimental Determination of Novel Formulation

Pre-formulation Studies
Ionic Strength Effects
Sodium Chloride Spiking

Ionic strength effects were evaluated with Composition 1 (50 mg/mL in PMTT (which comprises 10 mM phosphate, 200 mM mannitol, 60 mM trehalose and 0.01% PS80, at pH 7.2)) at six target sodium chloride concentrations (5 mM, 10 mM, 20 mM, 50 mM, 80 mM, 120 mM).

Vials of each sample were incubated at 25° C. for 5 days. Samples were removed from incubation after 5 days. The samples were compared to the 0 day and 0 mM sodium chloride controls by visual inspection and SE-HPLC.

The results suggest that increased concentrations of sodium chloride reduce purity loss. At or above 6 mS/cm, there is no significant change in SE-HPLC purity (FIG. 1, Table 1). All tested samples were clear, pale yellow, and essentially free from foreign particulate matter.

TABLE 1

Ionic Strength Effects Measured by Sodium Chloride Spiking.

| NaCl (mM) | Day | SE-HPLC purity (%) | SE-HPLC purity loss (%) |
|---|---|---|---|
| 0 | 0 | 99.8 | NA |
|   | 5 | 95.1 | −4.7 |
| 5 | 0 | 99.8 | NA |
|   | 5 | 95.9 | −3.9 |
| 10 | 0 | 99.8 | NA |
|   | 5 | 96.0 | −3.8 |
| 20 | 0 | 99.9 | NA |
|   | 5 | 96.3 | −3.6 |
| 50 | 0 | 99.8 | NA |
|   | 5 | 99.7 | −0.1 |
| 80 | 0 | 99.8 | NA |
|   | 5 | 99.7 | −0.1 |
| 120 | 0 | 99.8 | NA |
|   | 5 | 99.8 | 0.0 |

Buffer controls containing 5 mM, 10 mM, 20 mM, 50 mM, 80 mM, and 120 mM sodium chloride were measured for conductivity. Buffer controls containing 10 mM, 20 mM, 30 mM, 40 mM, 50 mM, and 60 mM phosphate were measured for conductivity.

Figure 2:
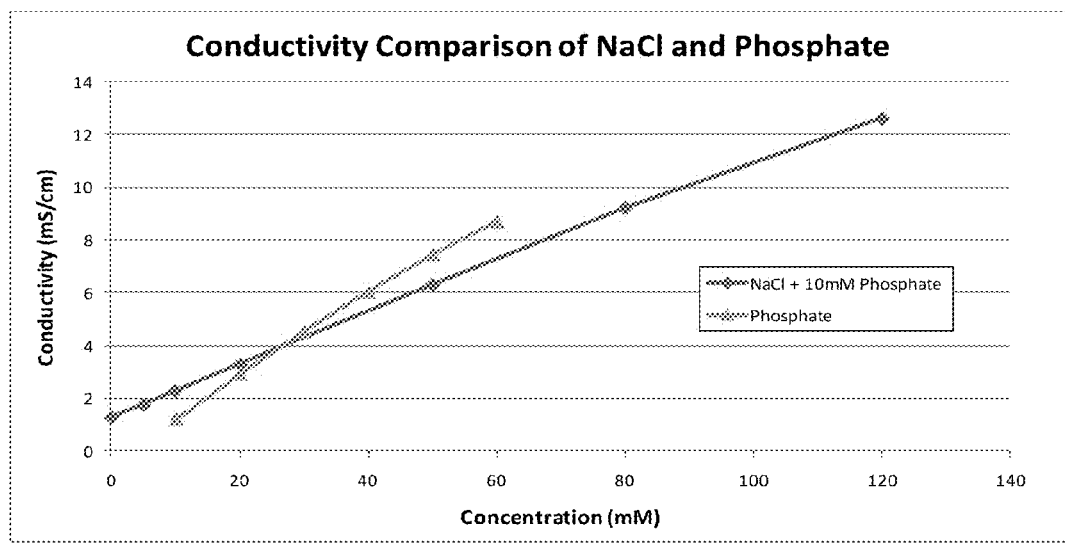
FIG. 2: Conductivity comparison of sodium chloride and sodium phosphate. The conductivity of sodium phosphate is greater than 6 mS/cm when the concentration is at least 50 mM.

When the concentration of phosphate is 50 mM, the conductivity of the solution is 6 mS/cm (FIG. 2, Table 2). Therefore, phosphate can be used to replace NaCl while maintaining the ionic strength.

TABLE 2

Sodium Chloride and Sodium Phosphate Buffer Conductivity Comparison.

| NaCl (mM) | Conductivity (mS/cm) | Phosphate (mM) | Conductivity (mS/cm) |
|---|---|---|---|
| 0 | 1.29 | 10 | 1.21 |
| 5 | 1.78 | 20 | 2.93 |
| 10 | 2.30 | 30 | 4.52 |
| 20 | 3.30 | 40 | 6.06 |
| 50 | 6.32 | 50 | 7.46 |
| 80 | 9.21 | 60 | 8.71 |
| 120 | 12.62 | | |

Phosphate Spiking

Ionic strength effects were evaluated with Composition 1 (100 mg/mL in 200 mM mannitol, 60 mM trehalose, 0.03% PS80, pH 7.2) at six target phosphate concentrations (10 mM, 20 mM, 30 mM, 40 mM, 50 mM, 60 mM).

Vials of each sample were incubated at 25° C. for 5 days. Samples were removed from incubation after 3 and 5 days. The samples were compared to the 0 day controls by visual inspection and SE-HPLC. Buffer controls were measured for conductivity.

Figure 3:
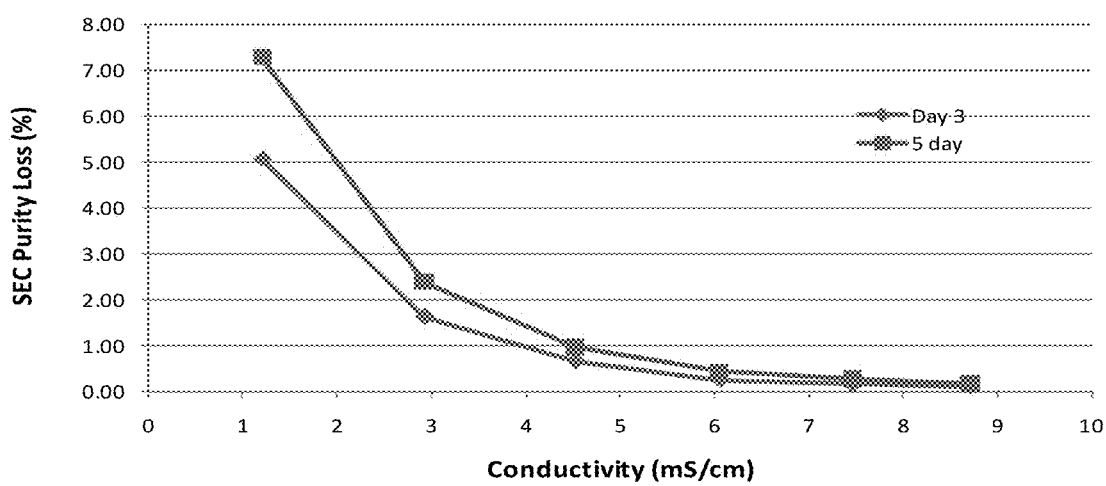
FIG. 3: The effect of ionic strength on the stability of Composition 1 in solution, as determined by sodium phosphate spiking. The stability of Composition 1 improves with increased conductivity.

The results show that increasing buffer conductivity decreases SE-HPLC purity loss. At a conductivity of approximately 4.5 mS/cm or higher (~≥30 mM sodium phosphate), there is no significant SE-HPLC purity loss after 5 days at 25° C. (FIG. 3, Table 3). All tested samples were clear, pale yellow, and essentially free from foreign particulate matter. Therefore, increasing ionic strength could prevent the protein from forming aggregates.

TABLE 3

Sodium Phosphate Spiking Data.

| Phosphate (mM) | Day | SE-HPLC purity (%) | SE-HPLC purity loss (%) |
|---|---|---|---|
| 10 | 0 | 99.6 | NA |
|  | 3 | 94.6 | −5.1 |
|  | 5 | 92.4 | −7.3 |
| 20 | 0 | 99.7 | NA |
|  | 3 | 98.0 | −1.6 |
|  | 5 | 97.3 | −2.4 |
| 30 | 0 | 99.7 | NA |
|  | 3 | 99.0 | −0.7 |
|  | 5 | 98.7 | −1.0 |
| 40 | 0 | 99.7 | NA |
|  | 3 | 99.4 | −0.3 |
|  | 5 | 99.2 | −0.4 |
| 50 | 0 | 99.6 | NA |
|  | 3 | 99.5 | −0.2 |
|  | 5 | 99.4 | −0.3 |
| 60 | 0 | 99.7 | NA |
|  | 3 | 99.6 | −0.1 |
|  | 5 | 99.5 | −0.2 |

Polysorbate 80 Effects

The effects of PS80 were evaluated with Composition 1 (100 mg/mL in 10 mM phosphate, 200 mM mannitol, 60 mM trehalose, pH 7.2) at four target PS80 concentrations (0.01%, 0.05%, 0.1%, and 0.2%). The samples were incubated at 2-8° C. and 25° C. for 1, 2 and 3 days. Samples were compared to the 0 point and the PS80-free controls by visual inspection and SE-HPLC. Osmolality was measured for the 0 points.

There was no change in purity for samples incubated at 2-8° C. (Table 4). Samples at 100 mg/ml in PMTT incubated at 25° C. showed 5-6% purity loss, but with no significant differences across the PS80 concentrations (Table 4). There was no change in appearance across all PS80 concentrations, temperatures and time points, with the reconstituted solution always a clear pale yellow liquid essentially free from foreign particulate matter. There was no change in osmolality (Table 5). Since there was no significant difference, 0.03% PS80, considered an acceptable middle point, was selected. This data also demonstrated that PMTT was not a suitable formulation for a higher dose of concentrated product.

TABLE 4

PS80 Spiking Purity Data

| Temperature | Day | SEC Purity (%) PS80 concentration (%) | | | | | SEC Purity Loss (%) PS80 concentration (%) | | | | |
|---|---|---|---|---|---|---|---|---|---|---|---|
| | | 0 | 0.01 | 0.05 | 0.1 | 0.2 | 0 | 0.01 | 0.05 | 0.1 | 0.2 |
| 2-8° C. | 0 | 99.7 | 99.7 | 99.8 | 99.8 | 99.7 | NA | NA | NA | NA | NA |
|  | 1 | 99.7 | 99.7 | 99.7 | 99.7 | 99.7 | 0.0 | 0.0 | −0.1 | 0.0 | 0.0 |
|  | 2 | 99.8 | 99.7 | 99.7 | 99.7 | 99.7 | 0.0 | 0.0 | −0.1 | 0.0 | 0.0 |
|  | 3 | 99.7 | 99.7 | 99.7 | 99.7 | 99.7 | 0.0 | 0.0 | 0.0 | −0.1 | 0.0 |
| 25° C. | 0 | 99.7 | 99.7 | 99.8 | 99.8 | 99.7 | NA | NA | NA | NA | NA |
|  | 1 | 97.5 | 97.5 | 97.6 | 97.6 | 97.6 | −2.2 | −2.2 | −2.2 | −2.1 | −2.1 |
|  | 2 | 95.5 | 95.5 | 95.6 | 95.8 | 95.8 | −4.2 | −4.3 | −4.1 | −4.0 | −3.9 |
|  | 3 | 94.0 | 94.1 | 94.1 | 94.3 | 94.3 | −5.7 | −5.6 | −5.7 | −5.5 | −5.5 |

TABLE 5

PS80 Spiking Osmolality Data
Osmolality Average (mOsm/kg)
PS80 concentration (%)

| 0 | 0.01 | 0.05 | 0.1 | 0.2 |
|---|---|---|---|---|
| 340 | 341 | 345 | 341 | 347 |

Buffer Composition

Formulation buffers containing varying concentrations of phosphate (40 mM, 50 mM and 60 mM), mannitol (60-200 mM), trehalose (18-60 mM) and 0.03% PS80 were made by combining varying amounts of 500 mM phosphate (pH 7.2) stock solution, 500 mM mannitol stock solution and 200 mM trehalose stock solution, while keeping the ratio of trehalose to mannitol the same as PMTT. The osmolality of each buffer was tested and compared to the osmolality of PMTT (Table 6).

TABLE 6

Phosphate Buffer Combinations

| PS80 (%) | Phosphate (mM) | Mannitol (mM) | Trehalose (mM) | Osm Average (mOsm/kg) |
|---|---|---|---|---|
| 0.01 | 10 | 200 | 60 | 309 |
| 0.03 | 40 | 200 | 60 | 417 |
| 0.03 | 40 | 160 | 48 | 360 |
| 0.03 | 40 | 154 | 46 | 352 |
| 0.03 | 40 | 150 | 45 | 342 |
| 0.03 | 40 | 146 | 44 | 341 |
| 0.03 | 40 | 140 | 42 | 355 |
| 0.03 | 40 | 120 | 36 | 308 |
| 0.03 | 40 | 114 | 34 | 299 |
| 0.03 | 40 | 110 | 33 | 294 |
| 0.03 | 40 | 106 | 32 | 289 |
| 0.03 | 40 | 100 | 30 | 281 |
| 0.03 | 50 | 200 | 60 | 454 |
| 0.03 | 50 | 150 | 45 | 381 |
| 0.03 | 50 | 146 | 44 | 378 |
| 0.03 | 50 | 140 | 42 | 367 |
| 0.03 | 50 | 134 | 40 | 365 |
| 0.03 | 50 | 130 | 39 | 356 |
| 0.03 | 50 | 100 | 30 | 315 |
| 0.03 | 50 | 94 | 28 | 306 |
| 0.03 | 50 | 90 | 27 | 301 |
| 0.03 | 50 | 86 | 26 | 297 |
| 0.03 | 50 | 80 | 24 | 285 |
| 0.03 | 60 | 200 | 60 | 484 |
| 0.03 | 60 | 134 | 40 | 406 |
| 0.03 | 60 | 130 | 39 | 384 |
| 0.03 | 60 | 126 | 38 | 382 |
| 0.03 | 60 | 120 | 36 | 372 |
| 0.03 | 60 | 114 | 34 | 363 |

TABLE 6-continued

Phosphate Buffer Combinations

| PS80 (%) | Phosphate (mM) | Mannitol (mM) | Trehalose (mM) | Osm Average (mOsm/kg) |
|---|---|---|---|---|
| 0.03 | 60 | 110 | 33 | 361 |
| 0.03 | 60 | 80 | 24 | 318 |
| 0.03 | 60 | 74 | 22 | 313 |
| 0.03 | 60 | 70 | 21 | 308 |
| 0.03 | 60 | 66 | 20 | 303 |
| 0.03 | 60 | 60 | 18 | 297 |

Buffers with osmolality approximately equal to 300 mOsm/kg were made, and conductivity and osmolality were measured for the buffers and for Composition 1 (100 mg/mL in PMTT) (Table 7).

TABLE 7

Proto-formulation Buffer Measurements (Bolded lines indicate P50MTT and P60MTT)

| Sample | Phosphate (mM) | Mannitol (mM) | Trehalose (mM) | PS80 (%) | pH | Osm Average (mOsm/kg) | Conductivity Average (mS/cm) |
|---|---|---|---|---|---|---|---|
| Buffer | 10 | 200 | 60 | 0.01 | 7.23 | 302 | 1.29 |
| Buffer | 10 | 200 | 60 | 0.01 | NT | 311 | NT |
| Composition 1 (100 mg/mL) | 10 | 200 | 60 | 0.01 | NT | 338 | NT |
| Buffer | 40 | 114 | 34 | 0.03 | 7.18 | 243 | NT |
| Buffer | 40 | 132 | 40 | 0.03 | 7.24 | 267 | 4.55 |
| Buffer | 40 | 146 | 44 | 0.03 | 7.20 | 289 | 4.46 |
| Buffer | 40 | 150 | 45 | 0.03 | 7.19 | 293 | 4.46 |
| Buffer | 50 | 90 | 27 | 0.03 | 7.20 | 232 | NT |
| Buffer | 50 | 94 | 28 | 0.03 | 7.20 | 235 | NT |
| Buffer | 50 | 115 | 35 | 0.03 | 7.18 | 267 | 5.54 |
| Buffer | 50 | 116 | 35 | 0.03 | 7.18 | 272 | 5.61 |
| Buffer | 50 | 134 | 40 | 0.03 | 7.25 | 294 | 5.52 |
| Buffer | 50 | 140 | 42 | 0.03 | 7.16 | 302 | 5.23 |
| Buffer | 60 | 60 | 18 | 0.03 | 7.20 | 211 | NT |
| Buffer | 60 | 66 | 20 | 0.03 | 7.18 | 219 | NT |
| Buffer | 60 | 100 | 30 | 0.03 | 7.21 | 268 | 6.59 |
| Buffer | 60 | 104 | 31 | 0.03 | 7.16 | 275 | 6.56 |
| Buffer | 60 | 120 | 36 | 0.03 | 7.21 | 290 | 6.31 |
| Buffer | 60 | 126 | 38 | 0.03 | 7.18 | 301 | 6.42 |

From measuring Composition 1 (100 mg/mL in PMTT) and PMTT alone, it was calculated that Composition 1 at 100 mg/mL contributes approximately 31.5 mOsm/kg to osmolality. Targeting an osmolality of 300 mOsm/kg, two formulations were selected: P50MTT (267 mOsm/kg), and P60MTT (268 mOsm/kg). P50MTT comprises 50 mM sodium phosphate, 115 mM mannitol, 35 mM trehalose and 0.03% PS80, at pH 7.2, while P60MTT comprises 60 mM phosphate, 100 mM mannitol, and 30 mM trehalose and 0.03% PS80, at pH 7.2.

Measurements were performed for Composition 1 (100 mg/mL) in the new P50MTT and P60MTT formulations (Table 8).

TABLE 8

P50MTT and P60MTT Measurements

| Formulation | Conductivity (mS/cm) | Osmolality buffer (mOsm/kg) | Osmolality sample (100 mg/ml) (mOsm/kg) | Density buffer (g/cm$^3$) | pH buffer |
|---|---|---|---|---|---|
| P50MTT | 5.75 | 274 | 307 | 1.015 | 7.09 |
| P60MTT | 6.77 | 272 | 306 | 1.015 | 7.09 |

Pre-Formulation Conclusions

The pre-formulation studies were executed to determine potential formulation candidates for the lyophilization formulation of the concentrated product. Previous studies showed that Composition 1 was affected by concentration dependent aggregation, suggesting that aggregation is a major degradation pathway.

In response, the ionic strength study was conducted to determine if increasing the ionic strength of the formulation buffer would have an effect on reducing aggregation. The results of the study demonstrate that there is a significant ionic strength effect, and in the higher ionic strength formulation there was a significant reduction in dose dependent aggregation at a protein concentration of 100 mg/ml.

The results of the PS80 spiking study show no difference between PS80 concentrations. Therefore, 0.03% PS80, which is within the acceptable range, was selected for the formulations.

Mannitol and trehalose concentrations in the candidate formulations were modified to target an osmolality of 300 mOsm/kg, while maintaining the ratio between mannitol and trehalose as established during development of the previous PMTT formulation. Two proto-formulations, P50MTT and P60MTT, were selected for additional studies.

Proto-Formulation Evaluation

Freeze-Thaw Effects

The effects of repeated freezing and thawing were evaluated with Composition 1 (101.6 mg/mL in P50MTT and 100.8 mg/mL in P60MTT). Samples were frozen for 2-16 hours at −65° C. and then thawed for 3 hours at room temperature. Samples were collected after 1, 2, 4, 6 and 10 complete cycles of freezing and thawing. Samples were compared to the 0 point by visual inspection and SE-HPLC. Select samples were also tested by SDS-PAGE and potency analysis.

The results show no change in SE-HPLC purity after 10 cycles of freeze and thaw on Composition 1 in both P50MTT and P60MTT. The SDS-PAGE results support the results of SE-HPLC. All tested samples were clear, pale yellow, and essentially free from foreign particulate matter. There was no significant change in potency (Table 9).

TABLE 9

Freeze-Thaw Effects on Composition 1

| Formulation | Cycle | SEC % Purity Average | SE-HPLC Purity Change (%) | Potency (%) |
|---|---|---|---|---|
| P50MTT | 0 | 99.3 | NA | 166 |
|  | 1 | 99.3 | 0.0 | NT |
|  | 2 | 99.4 | 0.1 | NT |
|  | 4 | 99.4 | 0.1 | NT |
|  | 6 | 99.4 | 0.1 | NT |
|  | 10 | 99.4 | 0.1 | 137 |
| P60MTT | 0 | 99.5 | NA | 145 |
|  | 1 | 99.4 | 0.0 | NT |
|  | 2 | 99.4 | 0.0 | NT |
|  | 4 | 99.4 | −0.1 | NT |
|  | 6 | 99.4 | 0.0 | NT |
|  | 10 | 99.4 | −0.1 | 138 |

Shaking Effects

The effects of shaking-induced aggregation were evaluated with Composition 1 (101.6 mg/mL in P50MTT and 100.8 mg/mL in P60MTT). Samples were shaken horizontally at 150 rpm. Samples were incubated at 2-8° C. and 25° C. from 0 to 24 hours. Samples were compared to the 0 point by visual inspection, SE-HPLC and HI-HPLC.

The results show no change in SE-HPLC purity or HI-HPLC purity for Composition 1 in both P50MTT and P60MTT. All tested samples were clear, pale yellow, and essentially free from foreign particulate matter. This suggests that Composition 1 is not sensitive to shaking induced aggregation (Table 10).

TABLE 10

Shaking Effects on Composition 1.

| Formulation | Temp | Hrs | SE-HPLC Purity (%) | SE-HPLC Purity Change (%) | HI-HPLC Purity (%) | HI-HPLC Purity Change (%) |
|---|---|---|---|---|---|---|
| P50MTT | 2-8° C. | 0 | 99.5 | NA | 91.5 | NA |
|  |  | 1 | 99.5 | 0.0 | NT | NT |
|  |  | 3 | 99.6 | 0.1 | 91.6 | 0.1 |
|  |  | 6 | 99.5 | 0.0 | NT | NT |
|  |  | 12 | 99.5 | 0.0 | 91.6 | 0.1 |
|  |  | 24 | 99.5 | 0.0 | 91.6 | 0.1 |
|  | 22° C. | 0 | 99.5 | NA | 91.5 | NA |
|  |  | 1 | 99.4 | 0.0 | NT | NT |
|  |  | 3 | 99.5 | 0.0 | 91.7 | 0.2 |
|  |  | 6 | 99.5 | 0.0 | NT | NT |
|  |  | 12 | 99.4 | 0.0 | 91.6 | 0.1 |
|  |  | 24 | 99.4 | −0.1 | 91.6 | 0.1 |
| P60MTT | 2-8° C. | 0 | 99.5 | NA | 91.7 | NA |
|  |  | 1 | 99.5 | 0.0 | NT | NT |
|  |  | 3 | 99.5 | 0.0 | 91.7 | 0.0 |
|  |  | 6 | 99.5 | 0.0 | NT | NT |
|  |  | 12 | 99.5 | 0.0 | 91.6 |  |
|  |  | 24 | 99.5 | 0.0 | 91.7 | 0.0 |
|  | 22° C. | 0 | 99.5 | NA | 91.7 | NA |
|  |  | 1 | 99.505 | 0.0 | NT | NT |
|  |  | 3 | 99.525 | 0.0 | 91.6 | −0.1 |
|  |  | 6 | 99.505 | 0.0 | NT | NT |
|  |  | 12 | 99.5 | 0.0 | 91.6 | −0.1 |
|  |  | 24 | 99.48 | 0.0 | 91.7 | 0.0 |

Short-Term Liquid Stability

Composition 1 (101.6 mg/mL P50MTT and 100.8 mg/mL in P60MTT) was used for this study. Samples were incubated at 2-8° C. and 25° C. for 6 days. Samples were removed from incubation after 1, 3 and 6 days. Samples were compared to the 0 point by visual inspection, SE-HPLC and HI-HPLC. All tested samples were clear, pale yellow, and essentially free from foreign particulate matter. Select samples were also tested by SDS-PAGE and potency analysis (Table 11).

TABLE 11

Short Term Liquid Stability Results

| Formulation (100 mg/mL) | Temp | Day | SE-HPLC Purity (%) | SE-HPLC Purity Loss (%) | HI-HPLC Purity (%) | HI-HPLC Purity Loss (%) | Potency (%) |
|---|---|---|---|---|---|---|---|
| PMTT | 25° C. | 0 | 99.6 | NA | 88.9 | NA | NT |
|  |  | 5 | 95.1 | −4.5 | 81.7 | −7.2 | NT |
| P50MTT | 2-8° C. | 0 | 99.4 | NA | 92.0 | NA | 131 |
|  |  | 1 | 99.4 | 0.0 | NT | NT | NT |
|  |  | 3 | 99.4 | 0.0 | 91.9 | −0.1 | NT |
|  |  | 6 | 99.3 | 0.0 | 91.9 | −0.1 | 147 |
|  | 25° C. | 0 | 99.4 | NA | 92.0 | NA | 131 |
|  |  | 1 | 99.3 | −0.1 | NT | NT | NT |
|  |  | 3 | 99.2 | −0.2 | 92.0 | 0.0 | NT |
|  |  | 6 | 99.0 | −0.3 | 92.0 | 0.0 | 120 |
| P60MTT | 2-8° C. | 0 | 99.4 | NA | 92.0 | NA | 154 |
|  |  | 1 | 99.4 | 0.0 | NT | NT | NT |
|  |  | 3 | 99.4 | 0.0 | 92.1 | 0.1 | NT |
|  |  | 6 | 99.4 | 0.0 | 92.1 | 0.1 | 129 |
|  | 25° C. | 0 | 99.4 | NA | 92.0 | NA | 154 |
|  |  | 1 | 99.4 | 0.0 | NT | NT | NT |
|  |  | 3 | 99.2 | −0.2 | 92.1 | 0.1 | NT |
|  |  | 6 | 99.1 | −0.3 | 91.9 | −0.1 | 126 |

Figure 4:
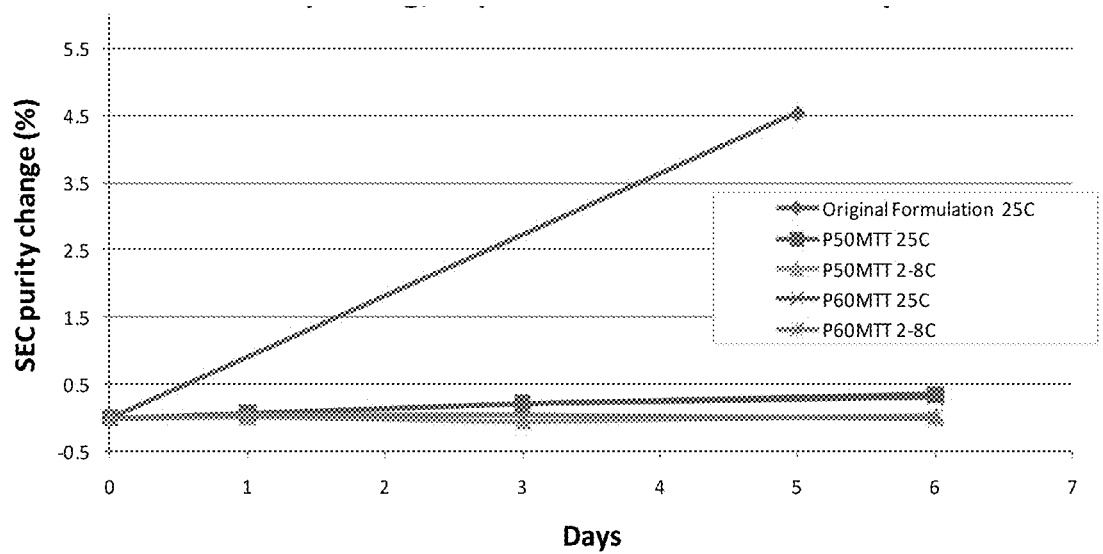
FIG. 4: The effects of various formulations on the stability of Composition 1 after incubation at 2-8° C. and 25° C. for 1, 3, and 6 days, measured by SE-HPLC. Both P50MTT and P60MTT provide better stability than PMTT.
Figure 5:
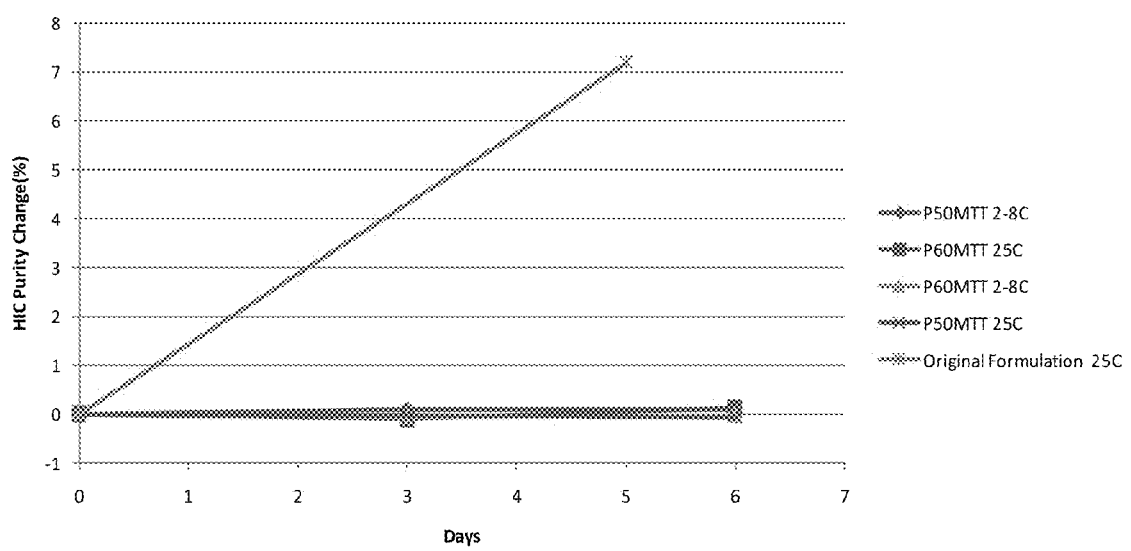
FIG. 5: The effects of various formulations on the stability of Composition 1 after incubation at 2-8° C. and 25° C. for 1, 3, and 6 days, measured by HI-HPLC. Both P50MTT and P60MTT provide better stability than PMTT.

The results show that Composition 1 in both P50MTT and P60MTT had no change in SE-HPLC (FIG. 4) and HI-HPLC purity (FIG. 5) after incubation in 2-8° C. and 25° C. for 6 days. This is a significant change from the prior formulation (PMTT), which had an approximate SE-HPLC purity loss of 4.5% and HI-HPLC purity loss of 7.2% after incubation at 25° C. after 5 days. The SDS-PAGE results support the results of SE-HPLC. There was no significant change in potency (Table 11).

Proto-Formulation Conclusion

The results of the proto-formulation studies indicate that Composition 1 at 100 mg/mL is stable at 2-8° C. and 25° C. for up to 6 days in both P50MTT and P60MTT formulations. Composition 1 in P50MTT and in P60MTT was not sensitive to freeze-thaw or shaking effects.

Overall, there was no difference between the P50MTT and P60MTT formulations. Both could support the lyophilization process and would be potential formulation candidates for an initial lyophilization evaluation.

Lyophilization Formulation Evaluation
Initial Lyophilization Evaluation

An initial lyophilization cycle evaluation was carried out using Composition 1 (101.6 mg/mL in P50MTT and 100.8 mg/mL in P60MTT). The TBU lyophilization cycle is summarized in Table 12. Post-lyophilization tests include visual inspection pre- and post-reconstitution and residual moisture content analysis. 0-12 hour post-reconstitution samples were analyzed by SE-HPLC and HI-HPLC. Selected samples were also tested by potency analysis.

TABLE 12

TBU Lyophilization Cycle

| Step | Parameters |
|---|---|
| a | Set the shelf temperature to 5° C. and load the samples. |
| b | Hold at 5° C. for 2 hours. |
| c | Ramp to −45° C. over 2.8 hours (0.3° C./min). |
| d | Hold at −45° C. for 3 hours. |
| e | Ramp to −18° C. over 0.6 hour (0.8° C./min). |
| f | Hold at −18° C. for 5 hours. |
| g | Ramp to −45° C. over 1.5 hours (0.3° C./min). |
| h | Hold at −45° C. for 2 hour. |
| i | Control pressure at 100 mT. |
| j | Hold at −45° C. for 1 hour. |
| k | Increase shelf temp to −10° C. over 0.8 hour (0.6° C./min). |
| l | Hold at −10° C. for 36 hours. |
| m | Increase shelf temp to 25° C. over 0.8 hour (0.6° C./min). |
| n | Hold at 25° C. for 15 hours. |
| o | Restore the chamber to partial atmospheric pressure. |
| p | Stopper the product. |

Figure 6:
FIG. 6: Lyophilization of Composition 1 produces pharmaceutically acceptable cakes in both P50MTT (left) and P60MTT (right).

The lyophilization products were, as shown in FIG. 6, pharmaceutically acceptable cakes (white to off-white in color and intact).

Figure 7:
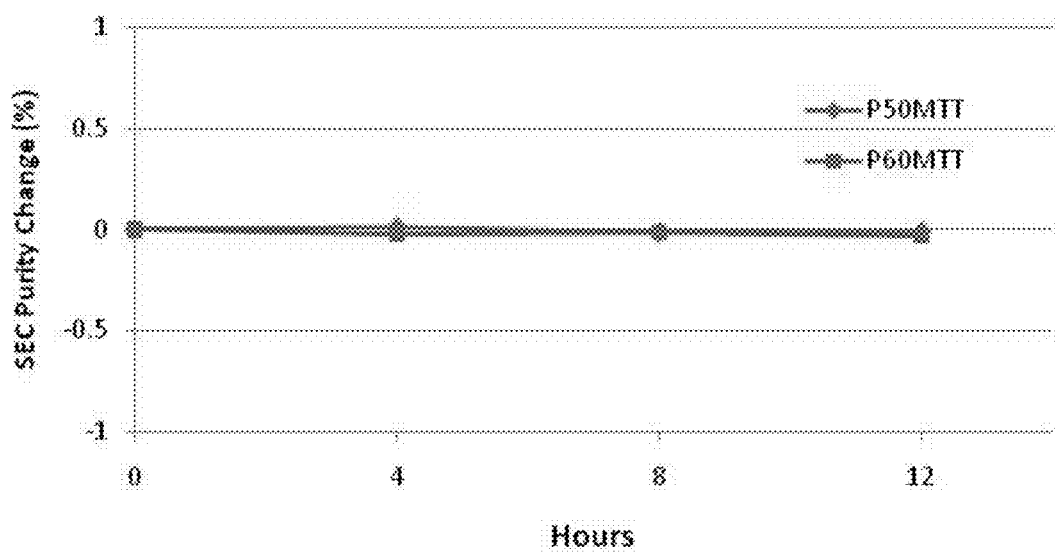
FIG. 7: The purity of reconstituted Composition 1, as measured by SE-HPLC at 0, 4, 8 and 12 hours after reconstitution. There was no substantial change in purity over time.
Figure 8:
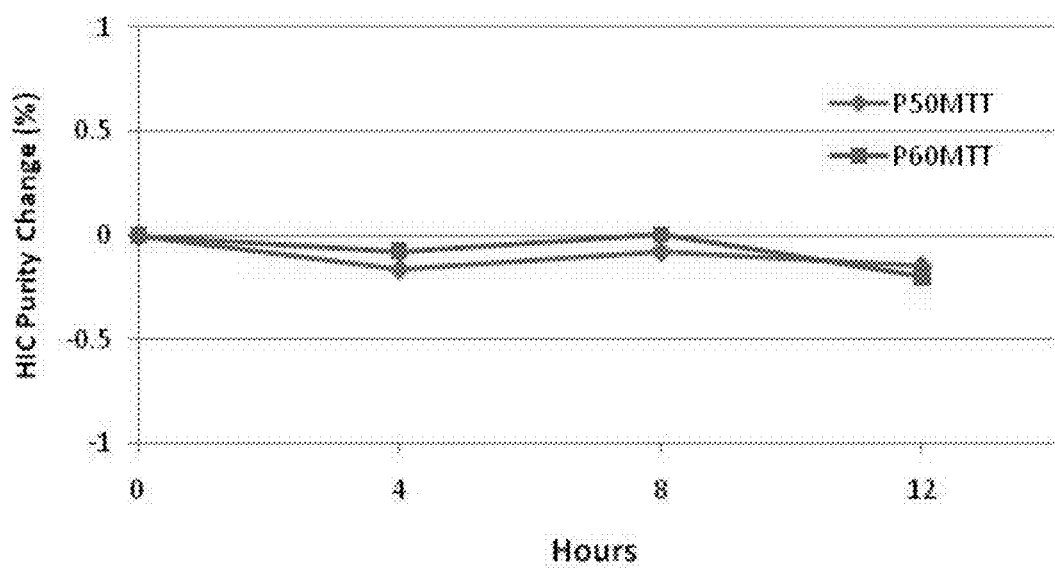
FIG. 8: The purity of reconstituted Composition 1, as measured by HI-HPLC at 0, 4, 8 and 12 hours after reconstitution. There was no substantial change in purity over time.
Figure 9:
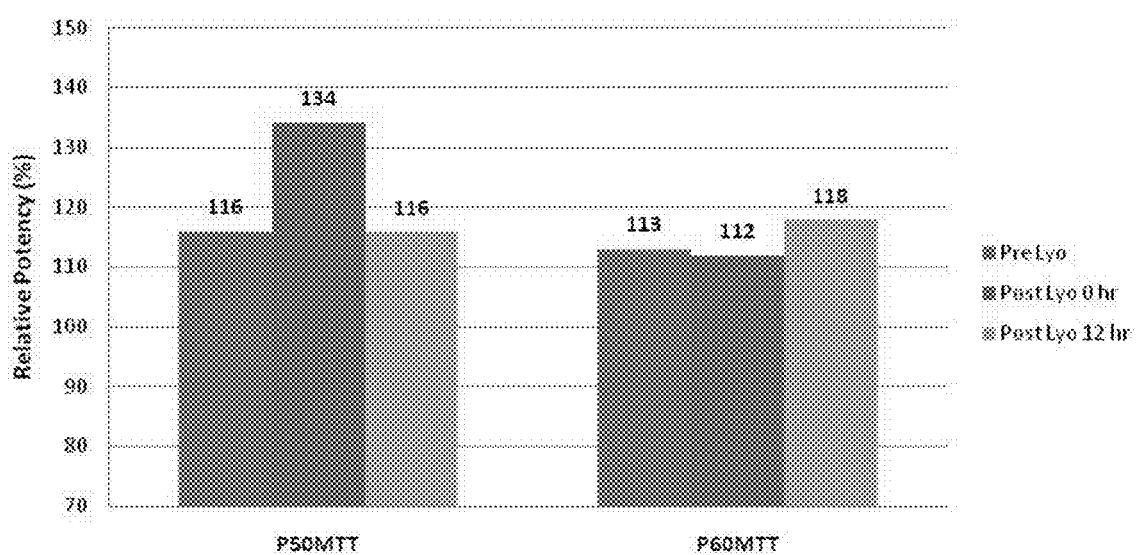
FIG. 9: The potency of Composition 1 before and after lyophilization, as measured at 0 and 12 hours after reconstitution. There was no substantial change in potency during the lyophilization process.

There was no change in SE-HPLC purity (FIG. 7), HI-HPLC purity (FIG. 8), and potency between pre- and post-lyophilization (FIG. 9). The residual moisture content for both cakes was 0.1%.

Lyophilization Cycle Evaluation
Low Temperature Thermal Analysis

To characterize the physio-chemical behavior of Composition 1 (100 mg/mL in P50MTT) at low temperatures, low temperature thermal analysis was performed. The analysis consisted of electrical resistance measurements (using a Kaye Validator instrument), observations of freeze drying behavior using a freeze-drying microscope (FDM), and low temperature differential scanning calorimetry (LT-DSC).

The results of the analysis are summarized below:
Phase transition at −17° C.
A minimum temperature of −29° C. is required for complete solidification
Liquid-like movement occurs at −4° C.
Recommended temperature for primary drying at or below a range of −6° C. to −8° C.

The TBU lyophilization cycle conditions are summarized as follows:
Freezing and refreezing steps at −45° C.
Annealing step at −18° C.
Primary drying at −10° C.

This data supports that the TBU lyophilization cycle is appropriately designed and suitable for this product.

TBU and Other Lyophilization Cycle Evaluations

Composition 1 (100 mg/mL in P50MTT) was lyophilized using the TBU cycle and used for the long term stability study.

Two randomly selected vials from the batch were analyzed by visual inspection and pre and post lyophilization analysis. The results indicate that the TBU cycle produces pharmaceutically acceptable cakes that are white to off-white in color and intact.

Additional lyophilization cycle evaluation was carried out using Composition 1 (103 mg/mL in P50MTT). A total of 7 development lyophilization cycles, as well as the TBU cycle as a control, were completed with variations to the freezing, annealing, primary drying, and secondary drying steps. Upon completion of the lyophilization process, samples were analyzed by visual inspection, moisture content analysis, HI-HPLC and SE-HPLC.

The lyophilization cycle evaluation was carried out using Composition 1 (103 mg/mL in P50MTT). Visual inspection, residual moisture content measurement, SE-HPLC and HI-HPLC purity analysis were performed. See Table 13 for detailed information pertaining to the various lyophilization cycle parameters.

TABLE 13

Lyophilization Cycle Parameters Summary

| Lyo Cycle | Shelf loading temp (C.) | Freezing Step (final temp, rate, hold duration) | Annealing Step (final temp, rate, hold duration) | Refreeze Step (final temp, rate, hold duration) | Primary drying (final temp, rate, hold duration, pressure) | Secondary drying final temp, rate, hold duration, pressure) | Total cycle time (hrs) |
|---|---|---|---|---|---|---|---|
| TBU | 5 | −45° C., 0.3° C./min, 3 hours | −18° C., 0.8° C./min, 5 hours | −45° C., 0.3° C./min, 2 hours | −45° C., 0.0° C./min, 1 hour, −10° C., 0.8° C./min, 36 hours, 100 mTorr | 25° C., 0.8° C./min, 15 hour, 100 mTorr | 70 |
| 1@ | 10 | −45° C., 0.5° C./min, 2 hours | — | — | −10° C., 0.2° C./min, 13 hours, 150 mTorr | 25° C., 0.3° C./min, 4 hour, 150 mTorr | 25 |

TABLE 13-continued

Lyophilization Cycle Parameters Summary

| Lyo Cycle | Shelf loading temp (C.) | Freezing Step (final temp, rate, hold duration) | Annealing Step (final temp, rate, hold duration) | Refreeze Step (final temp, rate, hold duration) | Primary drying (final temp, rate, hold duration, pressure) | Secondary drying final temp, rate, hold duration, pressure) | Total cycle time (hrs) |
|---|---|---|---|---|---|---|---|
| 2@ | 10 | −35° C., 0.6° C./min, 2 hours | −17° C., 0.3° C./min, 2 hours | −40° C., 0.4° C./min, 1 hour | −10° C., 0.2° C./min, 10 hours, 150 mTorr | 25° C., 0.3° C./min, 1 hour, 150 mTorr | 24.5 |
| 3# | 10 | −35° C., 0.6° C./min, 2 hours | −17° C., 0.3° C./min, 2 hours | −40° C., 0.4° C./min, 1 hour | −10° C., 0.2° C./min, 10 hours, 300 mTorr | 25° C., 0.3° C./min, 2 hours, 300 mTorr | 25.5 |
| 4# | 10 | −35° C., 0.4° C./min, 2 hours | −15° C., 0.3° C./min, 2 hours | −40° C., 0.4° C./min, 1 hour | −30° C., 0.2° C./min, 10 hours, −15° C., 0.1° C./min, 10 hours, 100 mTorr | 0° C., 0.5° C./min, 4.5 hours, 100 mTorr | 32 |
| 5# | 10 | −35° C., 0.6° C./min, 2 hours | −17° C., 0.3° C./min, 4 hours | −40° C., 0.4° C./min, 2 hour | −10° C., 0.2° C./min, 11 hours, 500 mTorr | 25° C., 0.6° C./min, 1 hour, 500 mTorr | 27.5 |
| 6# | 10 | −35° C., 0.3° C./min, 2 hours | −15° C., 0.3° C./min, 4 hours | −40° C., 0.2° C./min, 2 hour | −10° C., 0.1° C./min, 11 hours, 500 mTorr | 25° C., 0.3° C./min, 5 hour, 500 mTorr | 32.5 |
| 7# | −40 | −40° C., 4.25 hours | — | — | −10° C., 0.1° C./min, 12 hours, 500 mTorr | 25° C., 0.6° C./min, 5 hour, 500 mTorr | 25.25 |

The results of the lyophilization cycle evaluation further confirm that the TBU lyophilization cycle is more appropriate for Composition 1. The data suggests that the TBU cycle produces pharmaceutically acceptable cakes, with the lowest residual moisture (0.3%) compared to the other lyophilization cycles tested during the evaluation (Table 14).

TABLE 14

Lyophilization Cycle Evaluation Results Summary

| Lyo Cycle | General Cycle Parameters | Cake Appearance | Moisture content (% w/w) | Reconstitution time (min*) | Reconstituted product appearance, sample pH | Composition 1 concentration/purity HI-HPLC^ (mg/mL, %) | SE-HPLC^ (mg/mL, %) |
|---|---|---|---|---|---|---|---|
| TBU | Anneal at −18° C. for 5 h, primary at −10° C. for 36 h, 100 mT | White, intact cake, separation from vial side, slight top edge cracking | 0.3 | See Table 17 for TBU data | No particulates visible, color same as starting material, pH 7.10 | 98, 89.6 | 99, 99.5 |
| 1@ | Direct freeze to −45° C., primary at −10° C. for 13 h, 150 mT | White, intact cake, separation from vial side | 0.6 | 29.5 | No particulates visible, color same as starting material, pH 7.09 | 108, 90.3 | 100, 99.4 |
| 2@ | Anneal at −17° C. for 2 h, primary at −10° C. for 10 h, 150 mT | White, intact cake, slight separation from vial side, slight top edge cracking | 0.8 | 17.5 | No particulates visible, color same as starting material, pH 7.06 | 109, 90.8 | 102, 99.4 |
| 3# | Anneal at −17° C. for 2 h, primary at −10° C. for 10 h, 300 mT | White, intact cake, separation from vial side | 0.6 | 19.5 | No particulates visible, color same as starting material, pH 7.08 | 118, 90.4 | 113, 99.5 |
| 4# | Anneal at −15° C. for 2 h, primary at −30° C. for 10 h and −15° C. for 10 h, 100 mT | White, intact cake separation from vial side, slight top edge cracking | 0.6 | 24.0 | No particulates visible, color same as starting material, pH 7.09 | 118, 90.4 | 114, 99.5 |

TABLE 14-continued

Lyophilization Cycle Evaluation Results Summary

| Lyo Cycle | General Cycle Parameters | Cake Appearance | Moisture content (% w/w) | Reconstitution time (min*) | Reconstituted product appearance, sample pH | Composition 1 concentration/purity | |
|---|---|---|---|---|---|---|---|
| | | | | | | HI-HPLC^ (mg/mL, %) | SE-HPLC^ (mg/mL, %) |
| 5# | Anneal at −17° C. for 3 h, primary at −10° C. for 11 h, 500 mT | White, intact cake, contact with vial side, slight top edge cracking | 1.2 | 23.5 | No particulates visible, color same as starting material, pH 7.06 | 106, 89.6 | 108, 99.4 |
| 6# | Anneal at −15° C. for 4 h, 0.2° C./min warming rate to primary at −10° C., −10° C. for 11 h 500 mT | White, intact cake, contact with vial side, slight top edge cracking | 0.6 | 33.5 | No particulates visible, color same as starting material, pH 7.09 | NT | NT |
| 7# | Load samples on pre-cooled (−40° C.) helf, primary at −10° C. for 10 h, 500 mT | White, intact crystalline cake, separation from vial side | NT | 14 | No particulates visible, color same as starting material, pH 7.09 | 104, 91.0 | NT |

*Samples vials were reconstituted with 1 mL sWFI at ambient laboratory conditions. Samples were inverted 5X upon addition of sWFI and then incubated at ambient laboratory conditions without additional agitation until complete dissolution was observed.
@1.0 mL fill volume.
1.1 mL fill volume.
^Bulk TV-1380 purity 89.8%, 99.6% as determined by HIC and SEC-HPLC, respectively.

Pre- and Post-Lyophilization Analysis

Composition 1 (100 mg/ml in P50MTT after reconstitution with 1.1 ml of WFI) 0 month was used for the pre- and post-lyophilization analysis. Time points were 0, 4, 8 and 12 hours. Visual inspection was performed prior to reconstitution. Reconstitution time was recorded. Post-reconstitution, samples were analyzed by visual inspection, pH, osmolality, concentration measurement, SE-HPLC, SDS-PAGE, potency analysis and free thiol content (Table 15).

TABLE 15

Pre and Post Reconstitution Summary

| Attributes | Results | | | |
|---|---|---|---|---|
| | 0 hr | 4 hr | 8 hr | 12 hr |
| Appearance (Visual inspection - pre reconstitution; cake) | WC | WC | WC | WC |
| Appearance (Visual inspection - reconstitution time) | ≤4 min | ≤5 min | ≤5 min | ≤6 min |
| Appearance (Visual inspection - post reconstitution) | CYF | CYF | CYF | CYF |
| pH | 7.2 | 7.2 | 7.2 | 7.1 |
| Osmolality (Freezing point) (mOsm/kg) | 262 | 269 | 280 | 283 |
| Concentration (A280) (mg/mL) | 93.1 | 96.8 | 98.7 | 102.3 |
| Purity (SDS-PAGE), Reduced (%) | 100 | 100 | 100 | 100 |
| Purity (SDS-PAGE), Non-reduced (%) | 100 | 100 | 100 | 100 |
| Purity (SEC-HPLC) (%) | 99.1 | 99.0 | 99.1 | 99.1 |
| Potency (Esterase Activity) (%) | 113 (23.4 units/mg) | 127 (26.1 units/mg) | 125 (25.8 units/mg) | 129 (26.6 units/mg) |
| Free Thiol (mol/mol) | 1.6 | 1.5 | 1.6 | 1.6 |
| Sialic Acid Content (pmol/pmol) | NT | | | NT |

*Result is an average of vials taken from beginning, middle, and end of the lyo cycle The results indicate that the TBU cycle produces pharmaceutically acceptable cakes that are white to off-white in color and intact. Post reconstitution, samples are clear and free of particulate matter. Additionally, samples up to 12 hours post-reconstitution pass acceptance criteria (Tables 15, 16).

The pre-formulation studies demonstrated that increasing ionic strength results in a significant reduction in dose dependent aggregation at a protein concentration of 100 mg/ml. PS80 concentration had no significant effect and a concentration of 0.03% was selected for use in the proto-formulations.

TABLE 16

Acceptance Criteria

| Test | Analytical Method | Acceptance Criteria |
|---|---|---|
| Appearance (pre-reconstitution) | Visual inspection | White to off-white cake |
| Reconstitution time (reconstitute with 1.0 mL WFI) | | Report results (at minutes: ≤1 min if time needed is less than one minute) |
| Appearance (post-reconstitition) | | Clear to opalescent, pale yellow to yellow solution, essentially free from foreign particulate matter |
| pH | pH Electrode USP <791> Ph. Eur. 2.2.3 | 7.2 ± 0.4 |
| Osmolality | Freezing point USP <785> Ph. Eur. 2.2.35 | 300 ± 50 mOsm/kg |
| Purity | SDS-PAGE: Reduced and non-reduced with Coomassie blue stain | ≥90% |
| | SDS-PAGE: Reduced and non-reduced with Silver stain | Comparable to reference standard |
| | SE-HPLC | ≥90% |
| Potency | Esterase Assay | 15-29 units/mg protein |
| Identity | ELISA | Identity confirmed |
| Protein concentration (average of three values reported) | Absorbance at 280 nm | 100.0 ± 20.0 mg/mL |
| Sterility | USP <71> Ph. Eur. 2.6.1 | No growth |
| Bacterial Endotoxin | Kinetic turbidimetric USP <85> Ph. Eur. 2.6.14 | ≤1.200 EU/mg |
| Subvisible Particulate Matter | Light Obscuration USP <788> Ph. Eur. 2.9.19 | ≥10 μm NMT 6000 part/container ≥25 μm NMT 600 part/container |
| Residual Moisture (Three individual values reported) | Karl-Fischer Coulometer | ≤3.0% |

Conclusion of Lyophilization Evaluation

For essentially equivalent formulations, it is preferable to use the formulation containing a lower concentration of salt for the lyophilization process. Therefore, the P50MTT formulation was selected as the final concentrated product formulation and was used for the lyophilization formulation evaluation and long term stability program.

To summarize the lyophilization evaluation studies, the TBU lyophilization cycle is appropriate for the lyophilization of Composition 1. The results of the low thermal analysis study indicate that the parameters of the TBU lyophilization cycle meet the minimum temperature requirements and the pre and post lyophilization results suggest that there is no change in protein quality. Cakes produced using the TBU lyophilization cycle are white to off-white in color and are intact, which is considered to be pharmaceutically acceptable (FIG. 6).

The results of the lyophilization evaluation also suggest that the P50MTT is an appropriate formulation for the concentrated product. Upon reconstitution, samples remain clear and free of particulate matter.

Conclusion

The formulation studies were executed to determine an appropriate formulation for the lyophilized concentrated product.

Two proto-formulations, P50MTT and P60MTT, were selected for additional studies.

The study results indicates that Composition 1 drug substances at 100 mg/mL with these two formulations are stable at 2-8° C. and 25° C. for up to 6 days, and are neither sensitive to freeze-thaw nor shaking effects, which could support the lyophilization process. There is no significant impact on the product quality by post-lyophilization. Overall, the two formulations are comparable in terms of the product quality and stability.

However, the P50MTT formulation was selected as a formulation candidate for an additional lyophilization cycle evaluation and long term stability study, due to its lower ionic strength compared to P60MTT, which might negatively impact lyophilization process and lyophilization product.

The lyophilization evaluation studies support that the TBU cycle produces pharmaceutically acceptable cakes.

Overall, the results of the formulation studies demonstrate that P50MTT is a suitable lyophilization formulation for the concentrated product and the TBU lyophilization program would be an appropriate lyophilization process to use for concentrated product fill.

Example 2

Long Term Stability Testing

Methods

Composition 1 (100 mg/ml in P50MTT after reconstitution with 1.1 ml of WFI) was used for the stability program study. The lyophilized product was stored at 2-8° C., 25° C. and 40° C.

Results

At the end of 6 months, there is no significant change in SE-HPLC purity for Composition 1 when stored at 2-8° C. (Table 17). The quality attributes of samples stored at the recommended conditions meet all acceptance criteria up to 6 months. When stored at elevated temperature conditions, such as 25° C. and 40° C., there is a 2.5% and 9.6% loss in SE-HPLC purity after 6 months, respectively (Tables 18 and 19). However, there is no change in potency for all temperature conditions up to 6 months (Tables 17, 18 and 19).

TABLE 17

Stability Data for Composition 1 When Stored at Recommended Conditions, 2-8° C.

| Attributes | | Acceptance Criteria | Time (months) | | | | | | | |
|---|---|---|---|---|---|---|---|---|---|---|
| | | | 0 | 1 | 3 | 6 | 9 | 12 | 18 | 24 |
| Appearance (Pre-reconstitution) | | White to off-white cake | WC | WC | WC | WC | WC | WC | WC | WC |
| Appearance (Reconstitution time) | | Report results (≤X min) | 6 min | 7 min | 4 min | 6 min | 5 min | 5 min | 5 min | 5 min |
| Appearance (Post-reconstitution) | | Clear to opalescent, pale yellow to yellow solution, essentially free from foreign particulate matter | CYF | CYF | CYF | CYF | CYF | CYF | CYF | CYF |
| pH | | 7.2 ± 0.4 | 7.2 | 7.2 | 7.2 | 7.1 | 7.2 | 7.1 | 7.2 | 7.2 |
| Osmolality (Freezing point) | | 300 ± 50 mOsm/kg | 287 | 288 | 283 | 284 | 292 | 281 | 283 | 296 |
| Protein Concentration ($A_{280}$) | | 100 ± 20 mg/mL | 100.2[1] | 95.8 | 96.7 | 96.5 | 97.4 | 104.5 | 102.5 | 100.8 |
| Purity (SDS-PAGE), Coomassie | Reduced | ≥90.0% | 100 | 100 | 100 | 100 | 99 | 98 | 98 | 99 |
| | Non-reduced | ≥90.0% | 100 | 100 | 100 | 100 | 99 | 98 | 98 | 99 |
| Purity (SEC-HPLC) | Main Peak | ≥90% | 99.4 | 99.3 | 99.2 | 99.1 | 98.9 | 98.7 | 98.7 | 98.6 |
| | RRT 0.60-0.78 | Report Results (X.X %) | 0.0 | 0.0 | 0.0 | 0.0 | 0.0 | 0.0 | 0.0 | 0.0 |
| | RRT 0.87 | Report Results (X.X %) | 0.3 | 0.4 | 0.5 | 0.6 | 0.7 | 1.0 | 1.0 | 1.1 |
| | RRT 1.09-1.28 | Report Results (X.X %) | 0.3 | 0.3 | 0.3 | 0.3 | 0.3 | 0.3 | 0.3 | 0.3 |
| Potency (Esterase Assay) | | 15-29 units/mg protein | 23.9 | 21.2 | 20.7 | 24.1 | 24.1 | 20.1 | 23 | 24 |
| Residual Moisture | | ≤3.0% | 0.4[1] | 0.5 | 0.7 | 0.6 | 0.9 | 0.8 | 0.6 | 0.8 |
| Purity (HIC-HPLC) | Main Peak | Report Results (X.X %) | 89.5 | 89.5 | 89.2 | 89.5 | 89.6 | 89.3 | 89.5 | 89.7 |
| | RRT 1.09 | Report Results (X.X %) | 9.1 | 9.0 | 9.1 | 9.2 | 9.1 | 9.0 | 9.1 | 9.0 |
| Free Thiol (Ellman's Assay) | | Report Results (X.X mol/mol) | 1.5 | | | 1.8 | | 1.5 | | 1.7 |
| Sialic Acid Content | | Report Results (X.X pmol/pmol) | 8.8 | | | | | 9.7 | | |
| Deamidation | | Report Results (X.X pmol/pmol) | NT | | | | | 0.0175 | | 0.0193 |

WC = White Cake,
CYF = Clear, Yellow solution, essentially free from foreign particulate matter
[1]Result is an average of 3 vials (1 each from beginning, middle, and end)

TABLE 18

Stability Data for Composition 1, 25° C.

| Attributes | Time (months) | | | | | |
|---|---|---|---|---|---|---|
| | 0 | 1 | 3 | 6 | 9 | 12 |
| Appearance (Pre-reconstitution) | WC | WC | WC | WC | WC | WC |
| Appearance (Reconstitution time) | 6 min | 8 min | 5 min | 6 min | 5 min | 4 min |
| Appearance (Post-reconstitution) | CYF | CYF | CYF | CYF | CYF | CYF |
| pH | 7.2 | 7.2 | 7.2 | 7.1 | 7.2 | 7.2 |
| Osmolality (Freezing point) (mOsm/kg) | 287 | 287 | 296 | 288 | 285 | 294 |
| Protein Concentration ($A_{280}$) (mg/mL) | 100.2[1] | 96.8 | 95.2 | 96.4 | 98.5 | 102.7 |
| Purity   Reduced (%) | 100 | 99 | 99 | 98 | 97 | 98 |

TABLE 18-continued

Stability Data for Composition 1, 25° C.

| Attributes | | Time (months) | | | | | |
|---|---|---|---|---|---|---|---|
| | | 0 | 1 | 3 | 6 | 9 | 12 |
| (SDS-PAGE), Coomassie | Non-reduced (%) | 100 | 100 | 99 | 98 | 97 | 96 |
| Purity (SEC-HPLC) | Main Peak (%) | 99.4 | 98.6 | 97.8 | 97.1 | 96.4 | 95.9 |
| | RRT 0.60-0.78 (%) | 0.0 | 0.0 | 0.0 | 0.0 | 0.1 | 0.0 |
| | RRT 0.87 (%) | 0.3 | 1.1 | 1.8 | 2.5 | 3.2 | 3.8 |
| | RRT 1.09-1.28 (%) | 0.3 | 0.3 | 0.3 | 0.3 | 0.3 | 0.4 |
| Potency (Esterase Assay) (units/mg protein) | | 23.9 | 20.7 | 24.0 | 23.1 | 24.2 | 18.0 |
| Purity (HIC-HPLC) | Main Peak (%) | 89.5 | 89.6 | 88.9 | 89.4 | 89.8 | 89.4 |
| | RRT 1.09 (%) | 9.1 | 8.9 | 9.2 | 9.2 | 8.6 | 8.6 |
| Free Thiol (Ellman's Assay) (mol/mol) | | 1.5 | | | 1.8 | | 1.5 |
| Sialic Acid Content (pmol/pmol) | | 8.8 | | | | | 10.1 |
| Deamidation (pmol/pmol) | | NT | | | | | 0.0169 |

WC = White Cake,
CYF = Clear, Yellow solution, essentially free from foreign particulate matter
[1]Result is an average of 3 vials (1 each from beginning, middle, and end)

TABLE 19

Stability Data for Composition 1, 40° C.

| Attributes | | Time (months) | | | |
|---|---|---|---|---|---|
| | | 0 | 1 | 3 | 6 |
| Appearance (Pre-reconstitution) | | WC | WC | WC | WC |
| Appearance (Reconstitution time) | | 6 min | 8 min | 5 min | 6 min |
| Appearance (Post-reconstitution) | | CYF | CYF | CYF | CYF |
| pH | | 7.2 | 7.2 | 7.2 | 7.1 |
| Osmolality (Freezing point) (mOsm/kg) | | 287 | 283 | 283 | 288 |
| Protein Concentration ($A_{280}$) (mg/mL) | | 100.2[1] | 95.8 | 94.4 | 96.4 |
| Purity (SDS-PAGE), Coomassie | Reduced (%) | 100 | 97 | 93 | 93 |
| | Non-reduced (%) | 100 | 97 | 94 | 93 |
| Purity (SEC-HPLC) | Main Peak (%) | 99.4 | 96.4 | 93.8 | 91.1 |
| | RRT 0.60-0.78 (%) | 0.0 | 0.0 | 0.3 | 0.6 |
| | RRT 0.87 (%) | 0.3 | 1.1 | 5.6 | 8.0 |
| | RRT 1.09-1.28 (%) | 0.3 | 0.3 | 0.4 | 0.3 |
| Potency (Esterase Assay) (units/mg protein) | | 23.9 | 21.1 | 20.7 | 23.7 |
| Purity (HIC-HPLC) | Main Peak (%) | 89.5 | 89.7 | 89.0 | 88.4 |
| | RRT 1.09 (%) | 9.1 | 8.8 | 8.6 | 9.3 |
| Free Thiol(Ellman's Assay) (mol/mol) | | 1.5 | | | 1.7 |

WC = White Cake,
CYF = Clear, Yellow solution, essentially free from foreign particulate matter
[1]Result is an average of 3 vials (1 each from beginning, middle, and end)

Samples stored under recommended conditions are stable under the recommended conditions for 18 months.

Samples stored under recommended conditions are stable for 24 months.

Samples stored under recommended conditions are stable for 36 months.

Example 3

Production of Concentrated Product

Methods

Composition 1 has been predicted to be a glycosylated protein with N-linked glycosylation located at several sites on the catalytic domain of BChE. Composition 1 is constitutively secreted into the media during the growth of Chinese hamster ovary (CHO) cells that have been stably transfected with the gene for Composition 1. The protein is then purified through several orthogonal chromatographic and viral inactivation steps.

The cells are obtained from a working cell bank and cultured in a 1000 L batch. The medium contains 4 g/L, with a culture time of 16 days. Ultrafiltration-diafiltration is performed using a Cogent M1 TFFF System. Diafiltration is with 8 diafiltration volumes of buffer solution, to a target concentration of 110 mg of Composition 1 per millileter.

Results

The manufacturing processes of this example provides Composition 1 suitable for use in the methods disclosed herein.

Example 4

Administration to Humans

Methods

Samples of Composition 1 are prepared in P50MTT buffer and lyophilized. The samples are stored under the recommended conditions. The samples are reconstituted as needed, and the reconstituted solution is administered once weekly to humans seeking treatment for cocaine use. Administration is by intramuscular injection at doses of 150 or 300 mg, for a duration of 12 weeks.

Humans are included in the study if they are male or female aged 18-60 years (inclusive), meet Diagnostic and Statistical Manual of Mental Disorders, Fourth Edition, Text Revision (DSM-IV-TR) diagnostic criteria for cocaine dependence as determined by the Structured Clinical Interview (SCID), seek treatment for cocaine dependence, and provide at least four urine samples and have at least one cocaine-positive urine sample during the two-week screening period as measured by an on-site, qualitative benzoylecgonine (BE) assay (urine dipsticks).

Humans are excluded from participating in this study if they meet 1 or more of the following criteria:

a. Meet DSM-IV-TR criteria for current dependence on any psychoactive substance other than cocaine, alcohol, nicotine, benzodiazepines, or marijuana OR have physiological dependence on alcohol requiring detoxification.
b. Have most or all the available urine tests positive for opiates during the 2 weeks screening period (an episodic urine test positive for opiates is allowed).
c. Are currently treated with an opiate-substitute (buprenorphine or methadone) maintenance treatment or received therapy with any opiate-substitute within 90 days preceding screening.

d. Have one or more severe psychiatric disorders as determined by the Mini International Neuropsychiatric Interview (M.I.N.I.) such as psychosis, schizophrenia, bipolar disease, major depression, or eating disorders.
e. Have one or more major neurologic disorders such as dementia or organic brain disease.
f. Have other serious medical illnesses (including but not limited to uncontrolled hypertension, significant heart disease, respiratory disease including asthma, hepatic disease, renal disease, AIDS) or other potentially life threatening or progressive medical illness that may compromise subject safety or study conduct as determined by the site MD.
g. Had previous suicidal attempt or current suicidal risk.
h. Have liver function tests (ALT, AST) greater than ×3 times upper limit of normal (ULN) or any other clinically significant abnormal laboratory value during the screening period as determined by the site MD.
i. Have known allergy or hypersensitivity to natural or recombinant butyryl cholinesterase (BChE), human serum albumin (HSA) or any other component of the formulation.
j. Current court mandated cocaine use treatment.
k. Have been treated for cocaine addiction within the 30 days preceding screening.
l. Are unable to complete the study protocol because of probable incarceration or relocation from the clinical area.
m. Have taken any investigational drugs within 60 days preceding screening.
n. Have participated in an experimental trial assessing a cocaine vaccine anytime before study screening.
o. Are currently exposed to or have been exposed to pesticides or any other organophosphates (e.g., agricultural workers) within 60 days preceding screening.
p. Women of child-bearing potential who do not practice an acceptable method of birth control [acceptable methods of birth control in this study are: surgical sterilization, intrauterine devices, oral contraceptive, contraceptive patch, long-acting injectable contraceptive, a double-protection method (condom or diaphragm with spermicide)].
q. Pregnant or nursing women.

There is a screening period of up to 2 weeks including three sites visits per week (Visit 1-Visit 6). During the first screening visit (Visit 1), an informed consent is obtained before performing any study assessments or procedures. The assessments and procedures performed at Visit 1 include a comprehensive medical and psychiatric history, a record of previous medications, a full physical examination including measurements of vital signs, typical clinical laboratory tests (complete blood count, blood chemistries, liver function tests, urinalysis), urine pregnancy tests (if female), a 12-lead electrocardiogram (ECG) and samples for immunogenicity (antibodies against HSA, BChE, and Composition 1).

At the same visit, the DSM-IV-TR diagnosis of current cocaine dependence is verified with a Structured Clinical Interview (SCID) and other major psychiatric disorders are ruled out with the Mini-International Neuro-psychiatric Interview (M.I.N.I). The Beck Depression Index-II (BDI-II) is also completed at Visit 1. Urine samples for cocaine metabolites, benzoylecgonine (BE) and ecgonine methyl ester (EME) screening (quantitative assays) as well as urine samples for opiates, marijuana, amphetamine and benzodiazepine screening (dipsticks) are obtained at Visit 1 and at each one of the following screening visits (Visit 2-Visit 6). A sample for endogenous BChE and AChE activity level is collected during Visit 1. Physical examination including vital signs measurements is performed once during the second week of the screening.

At the end of the screening period (or as soon as at least one out of at least 4 urine samples is positive for EME and BE), eligible subjects are equally randomized on Day 0 (baseline, Visit 7 or earlier) to receive QW IM injection of Composition 1 150 mg, Composition 1 300 mg, or placebo for 12 weeks. During the baseline visit, the Addiction Severity Index (ASI), Brief Substance Craving Scale (BSCS), Social Adjustment Scale (SAS), Clinical Global Impression of disease severity (CGI-S), Clinical Global Impression of disease change (CGI-C), 36-item Short-Form Health Survey (SF-36), BDI-II scales and a timeline follow back (TLFB) are also completed.

There are three sites visits per week during the 12 weeks double-blind placebo-controlled treatment period (Visit 7-Visit 42). These visits occur on Mondays, Wednesdays and Fridays (if a subject cannot attend scheduled visits, attempts are made to see him/her on the subsequent day). Subjects are administered the study drug at Visit 7 and once a week during study visits, with the goal of administering the study drug on the same day of each week.

During each visit, the subject are asked using the TLFB to provide self-report of use/no use of cocaine during the days preceding the visit back to the previous visit.

In addition to the study drug, subjects in all three groups receive an individual, 1 hour manual-guided cognitive behavioral therapy session once-weekly during the treatment period. The manual used is NIDA's therapy manual titled "A cognitive behavioral approach: treating cocaine addiction."

To increase retention rate in the study during the treatment period and decrease rate of missing data for self-report of use/no use, a contingency management procedure is implemented.

Subjects are also instructed that self-report of cocaine use or urine containing cocaine metabolites does not affect drawings from the fish-bowl or participation in the trial.

There is a follow-up visit 4 weeks after the last study drug dose [End of Study (EoS) visit]. During this visit, a full physical examination including measurement of vital signs, clinical laboratory tests and urine pregnancy tests (if female) is performed. The ASI, BSCS, SAS, CGI-S, CGI-C, SF-36, BDI-II scales and a TLFB are also completed. Urine samples for BE and EME screening (quantitative assays) and urine samples for opiates, marijuana, amphetamine and benzodiazepine screening (dipsticks) are also obtained as well as samples for immunogenicity and endogenous BChE/AChE activity level. In subjects with a positive immunogenicity result at the end of the study (Visit 43, or 4 weeks after the last study drug dose in case of early termination), additional testing for antibodies is done 3-5 months after last study drug dose.

Primary Efficacy Endpoint:

The primary efficacy endpoint for this study is defined as abstinence from cocaine during the last three weeks of the treatment phase (weeks 10-12), based on daily self-report of no use confirmed by urine samples considered negative for cocaine metabolites.

Urine samples are collected thrice weekly during the treatment phase (on Mondays, Wednesdays and Fridays).

In order to consider a subject as abstinent during weeks 10-12, the following criteria are met:
1. Self-report of no use during each whole week
2. At least one analyzable urine sample is available during each of the above weeks 3. All urine samples provided during each of the above weeks are considered negative for cocaine metabolites (BE<150 ng/ml and EME<15 ng/ml)

In case no urine sample is provided or no analyzable urine sample is available during a single week (week 10, 11 or 12), it is considered that cocaine has been used for this specific week regardless of the information from self-report.

Secondary Efficacy Endpoint:

The secondary efficacy endpoint for this study is defined as the percent of urine samples that are considered negative for cocaine metabolites (BE<150 ng/ml and EME<15 ng/ml) out of all planned urine samples during weeks 5-12 of the treatment phase (24 samples).

Missing or not analyzable urine samples are considered as not negative for cocaine metabolites.

Exploratory Efficacy Endpoints:

Exploratory endpoints include change from baseline of various social and emotional scales.

Results

Administration of Composition 1 is safe and effective.

Administration of Composition 1 facilitates abstinence from cocaine in cocaine-dependent subjects.

Administration of Composition 1 induces abstinence from cocaine in the human for a time period of at least three weeks beginning ten weeks after the first administration of the composition to the human as part of the concurrent treatment regimen.

Administration of Composition 1 reduces the number of times a human uses cocaine in a time period of at least seven weeks beginning five weeks after the first administration of the composition to the human as part of the concurrent treatment regimen.

Administration of Composition 1 induces abstinence from cocaine in the human for a time period of at least seven weeks beginning five weeks after the first administration of the composition to the human as part of the concurrent treatment regimen.

Administration of Composition 1 reduces the human's cocaine craving, as measured by the human's BSCS score.

Administration of Composition 1 improves the human's Clinical Global Impression of disease severity, as assessed by the human and/or another observer twelve weeks after the first administration of the composition to the human as part of the concurrent treatment regimen.

Administration of Composition 1 improves the human's Clinical Global Impression of disease change, as assessed by the human and/or another observer twelve weeks after the first administration of the composition to the human as part of the concurrent treatment regimen.

Administration of Composition 1 improves the human's SAS twelve weeks after the first administration of the composition to the human as part of the concurrent treatment regimen.

Administration of Composition 1 improves the human's ASI twelve weeks after the first administration of the composition to the human as part of the concurrent treatment regimen.

Administration of Composition 1 improves the human's SF-36 twelve weeks after the first administration of the composition to the human as part of the concurrent treatment regimen.

Discussion

A previously disclosed formulation contained 30 mg/mL of Composition 1 in 10 mM phosphate, 200 mM mannitol, 60 mM trehalose and 0.01% PS80, pH 7.2 (PMTT) (U.S. Publication No. 2011/0312900 A1).

A more concentrated formulation can have significant advantages, including increasing convenience (since fewer or smaller vials are required to contain a given dose) and reducing the injection bolus necessary for a given dose. However, it is not always routine and often very difficult to increase the concentration of a peptide formulation. It is also recognized that changing excipients can change the efficacy of a composition, so it is desirable to use the same excipients in developing new formulations (Guidance for Industry: Submission of Summary Bioequivalence Data for ANDAs, 2009). Even so, it is unpredictable whether excipients suitable for preformulation products will effectively stabilize higher concentration products (Shire 2004).

The formulation of lyophilized proteins is not straightforward, and usually requires experimentation (Wang 2000; Shire 2004). Proteins tend to aggregate in a concentration-dependent manner (Wang 2005). The freezing necessary for lyophilization worsens this through cryoconcentration (Rathore and Rajan 2008).

The problem of aggregation during lyophilization is often addressed through adding preferentially excluded osmolytes. However, in some cases the addition of osmolytes has the opposite effect, increasing aggregation (Shire 2004).

Proteins generally need to be kept within a specific pH range, and therefore require a buffered solution, but "the effect of different buffering agents on long-term stability of lyophilized proteins is usually unpredictable" such that "selection of a buffering agent(s) can only rely on stability studies." (Wang 2000; see also Gokarn et al. 2006).

Furthermore, sodium phosphate is known to cause massive pH drops should $Na_2HPO_4$ selectively crystallize during lyophilization (Wang 2000; Wang 2005; Rathore and Rajan 2008; Frokjaer and Otzen 2005). The art also cautions that salt concentration should be kept to a minimum (Wang 2000).

Both mannitol and trehalose have a tendency to crystallize during freezing, preventing them from interacting with and stabilizing the protein (Shire 2009).

The appropriateness of a lyophilization process is also unpredictable. Freezing rates that are either too fast or too slow can lead to protein aggregation or denaturing (Rathore and Rajan 2008; Krishnamurthy and Manning 2002). Excessive drying can destabilize the protein (Rathore and Rajan 2008). Even the material used for the vial and the stopper can have critical effect on lyophilized protein products (Rathore and Rajan 2008).

The formulation described herein, however, represents an approach which manages issues associated with lyophilized protein formulations while satisfying the clinical need for a concentrated Composition 1 formulation suitable for lyophilization.

REFERENCES

Frokjaer, Sven, and Daniel E. Otzen. "Protein drug stability: a formulation challenge." Nature Reviews Drug Discovery 4.4 (2005): 298-306.

Gokarn, Yatin R., et al. "Excipients for protein drugs." Excipient Development for Pharmaceutical, Biotechnology, and Drug Delivery Systems (2006): 291.

Guidance for Industry: Submission of Summary Bioequivalence Data for ANDAs. U.S. Food and Drug Administration, Center for Drug Evaluation and Research (CDER). April 2009.

Krishnamurthy, Rajesh, and Mark C. Manning. "The stability factor: importance in formulation development." Current Pharmaceutical Biotechnology 3.4 (2002): 361-371.

Rathore, Nitin, and Rahul S. Rajan. "Current perspectives on stability of protein drug products during formulation, fill and finish operations." Biotechnology Progress 24.3 (2008): 504-514.

Shire, Steven J., Zahra Shahrokh, and Jun Liu. "Challenges in the development of high protein concentration formulations." Journal of Pharmaceutical Sciences 93.6 (2004): 1390-1402.

Shire, Steven J. "Formulation and manufacturability of biologics." Current opinion in biotechnology 20.6 (2009): 708-714.

Wang, Wei. "Lyophilization and development of solid protein pharmaceuticals." International Journal of Pharmaceutics 203.1 (2000): 1-60.

Wang, Wei. "Protein aggregation and its inhibition in biopharmaceutics." International journal of pharmaceutics 289.1 (2005): 1-30.

---

What is claimed is:

1. An aqueous pharmaceutical composition comprising a fusion protein and an aqueous solution comprising 40 to 60 mM sodium phosphate, 100 to 150 mM mannitol, 20 to 40 mM trehalose, and 0.02 to 0.05 percent polysorbate 80, wherein the pH of the aqueous solution is 6.9-7.5, wherein said fusion protein comprises the amino acid sequence of SEQ ID NO: 1, and wherein a concentration of said fusion protein is 80 to 120 mg/ml.

2. The aqueous pharmaceutical composition of claim 1, wherein said aqueous solution comprises 50 mM sodium phosphate, 115 mM mannitol, 35 mM trehalose, and 0.03 percent polysorbate 80.

3. The aqueous pharmaceutical composition of claim 1, wherein said concentration of said fusion protein is 100 mg/ml.

4. A pharmaceutical composition comprising a lyophilized form of the aqueous pharmaceutical composition of claim 1.

5. A reconstituted solution comprising the lyophilized form of claim 4 and a pharmaceutically acceptable solvent.

6. A sealed package comprising the pharmaceutical composition of claim 4.

7. A vial comprising the pharmaceutical composition of claim 4.

8. A method of producing a lyophilized pharmaceutical composition, comprising the steps of (i) obtaining the aqueous pharmaceutical composition of claim 1, and (ii) lyophilizing said aqueous pharmaceutical composition.

9. A method of producing a sealed package comprising a lyophilized pharmaceutical composition, comprising the steps of (i) obtaining the aqueous pharmaceutical composition of claim 1, (ii) placing said aqueous pharmaceutical composition in a container, (iii) lyophilizing said aqueous pharmaceutical composition, and (iv) sealing said container, thereby forming said sealed package.

10. A method of attenuating a biological effect of cocaine exposure in a human subject in need thereof comprising administering an effective amount of the aqueous pharmaceutical composition of claim 1 to said human subject, thereby attenuating said biological effect of cocaine exposure relative to a human subject without said effective amount of said aqueous pharmaceutical composition.

11. A method of attenuating a biological effect of cocaine exposure in a human subject in need thereof comprising the steps of (i) reconstituting the pharmaceutical composition of claim 4 by adding an amount of a pharmaceutically acceptable solvent to form a reconstituted solution, and (ii) administering an effective amount of said reconstituted solution to said human subject, thereby attenuating said biological effect of cocaine exposure relative to a human subject without said effective amount of said reconstituted solution.

12. A method of attenuating a biological effect of cocaine exposure in a human subject in need thereof comprising administering an effective amount of the reconstituted solution of claim 5 to said human subject, thereby attenuating said biological effect of cocaine exposure relative to a human subject without said effective amount of said reconstituted solution.

13. A method of attenuating a biological effect of cocaine exposure in a human subject in need thereof comprising the steps of (i) adding an amount of a pharmaceutically acceptable solvent to the sealed package of claim 6, to form a reconstituted solution, (ii) removing an effective amount of said reconstituted solution from said sealed package, and (iii) administering said effective amount of said reconstituted solution to said human subject, thereby attenuating said biological effect of cocaine exposure relative to a human subject without said effective amount of said reconstituted solution.

* * * * *

SEQUENCE LISTING

```
<160> NUMBER OF SEQ ID NOS: 1

<210> SEQ ID NO 1
<211> LENGTH: 1114
<212> TYPE: PRT
<213> ORGANISM: Artificial Sequence
<220> FEATURE:
<223> OTHER INFORMATION: AlbuBChE

<400> SEQUENCE: 1

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
        275                 280                 285
```

-continued

```
Asn Phe Gly Pro Thr Val Asp Gly Asp Phe Leu Thr Asp Met Pro Asp
        290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
        450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Asp Ala His Lys Ser Glu Val Ala His Arg Phe Lys Asp Leu Gly
        530                 535                 540

Glu Glu Asn Phe Lys Ala Leu Val Leu Ile Ala Phe Ala Gln Tyr Leu
545                 550                 555                 560

Gln Gln Cys Pro Phe Glu Asp His Val Lys Leu Val Asn Glu Val Thr
                565                 570                 575

Glu Phe Ala Lys Thr Cys Val Ala Asp Glu Ser Ala Glu Asn Cys Asp
                580                 585                 590

Lys Ser Leu His Thr Leu Phe Gly Asp Lys Leu Cys Thr Val Ala Thr
            595                 600                 605

Leu Arg Glu Thr Tyr Gly Glu Met Ala Asp Cys Cys Ala Lys Gln Glu
        610                 615                 620

Pro Glu Arg Asn Glu Cys Phe Leu Gln His Lys Asp Asp Asn Pro Asn
625                 630                 635                 640

Leu Pro Arg Leu Val Arg Pro Glu Val Asp Val Met Cys Thr Ala Phe
                645                 650                 655

His Asp Asn Glu Glu Thr Phe Leu Lys Lys Tyr Leu Tyr Glu Ile Ala
                660                 665                 670

Arg Arg His Pro Tyr Phe Tyr Ala Pro Glu Leu Leu Phe Phe Ala Lys
            675                 680                 685

Arg Tyr Lys Ala Ala Phe Thr Glu Cys Cys Gln Ala Ala Asp Lys Ala
        690                 695                 700
```

-continued

```
Ala Cys Leu Leu Pro Lys Leu Asp Glu Leu Arg Asp Glu Gly Lys Ala
705                 710                 715                 720

Ser Ser Ala Lys Gln Arg Leu Lys Cys Ala Ser Leu Gln Lys Phe Gly
                725                 730                 735

Glu Arg Ala Phe Lys Ala Trp Ala Val Ala Arg Leu Ser Gln Arg Phe
                    740                 745                 750

Pro Lys Ala Glu Phe Ala Glu Val Ser Lys Leu Val Thr Asp Leu Thr
                755                 760                 765

Lys Val His Thr Glu Cys Cys His Gly Asp Leu Leu Glu Cys Ala Asp
                770                 775                 780

Asp Arg Ala Asp Leu Ala Lys Tyr Ile Cys Glu Asn Gln Asp Ser Ile
785                 790                 795                 800

Ser Ser Lys Leu Lys Glu Cys Cys Glu Lys Pro Leu Leu Glu Lys Ser
                805                 810                 815

His Cys Ile Ala Glu Val Glu Asn Asp Glu Met Pro Ala Asp Leu Pro
                820                 825                 830

Ser Leu Ala Ala Asp Phe Val Glu Ser Lys Asp Val Cys Lys Asn Tyr
                835                 840                 845

Ala Glu Ala Lys Asp Val Phe Leu Gly Met Phe Leu Tyr Glu Tyr Ala
850                 855                 860

Arg Arg His Pro Asp Tyr Ser Val Val Leu Leu Leu Arg Leu Ala Lys
865                 870                 875                 880

Thr Tyr Glu Thr Thr Leu Glu Lys Cys Cys Ala Ala Ala Asp Pro His
                885                 890                 895

Glu Cys Tyr Ala Lys Val Phe Asp Glu Phe Lys Pro Leu Val Glu Glu
                900                 905                 910

Pro Gln Asn Leu Ile Lys Gln Asn Cys Glu Leu Phe Glu Gln Leu Gly
                915                 920                 925

Glu Tyr Lys Phe Gln Asn Ala Leu Leu Val Arg Tyr Thr Lys Lys Val
                930                 935                 940

Pro Gln Val Ser Thr Pro Thr Leu Val Glu Val Ser Arg Asn Leu Gly
945                 950                 955                 960

Lys Val Gly Ser Lys Cys Cys Lys His Pro Glu Ala Lys Arg Met Pro
                965                 970                 975

Cys Ala Glu Asp Tyr Leu Ser Val Val Leu Asn Gln Leu Cys Val Leu
                980                 985                 990

His Glu Lys Thr Pro Val Ser Asp Arg Val Thr Lys Cys Cys Thr Glu
                995                 1000                1005

Ser Leu Val Asn Arg Arg Pro Cys Phe Ser Ala Leu Glu Val Asp
                1010                1015                1020

Glu Thr Tyr Val Pro Lys Glu Phe Asn Ala Glu Thr Phe Thr Phe
                1025                1030                1035

His Ala Asp Ile Cys Thr Leu Ser Glu Lys Glu Arg Gln Ile Lys
                1040                1045                1050

Lys Gln Thr Ala Leu Val Glu Leu Val Lys His Lys Pro Lys Ala
                1055                1060                1065

Thr Lys Glu Gln Leu Lys Ala Val Met Asp Asp Phe Ala Ala Phe
                1070                1075                1080

Val Glu Lys Cys Cys Lys Ala Asp Asp Lys Glu Thr Cys Phe Ala
                1085                1090                1095
```

```
Glu Glu  Gly Lys Lys Leu Val  Ala Ala Ser Gln Ala  Ala Leu Gly
    1100             1105             1110
Leu
```